(12) United States Patent
Hew

(10) Patent No.: US 6,429,293 B1
(45) Date of Patent: Aug. 6, 2002

(54) SCULPIN-TYPE ANTIFREEZE POLYPEPTIDES AND NUCLEIC ACIDS

(75) Inventor: Choy L. Hew, Thornhill, CA (US)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 09/344,529

(22) Filed: Jun. 24, 1999

Related U.S. Application Data

(60) Provisional application No. 60/090,794, filed on Jun. 26, 1998, and provisional application No. 60/095,713, filed on Aug. 7, 1998.

(51) Int. Cl.$^7$ .......................... A23C 3/00; A61K 38/00; A61K 38/04; C07K 1/00
(52) U.S. Cl. ...................... 530/350; 426/321; 530/300; 530/327
(58) Field of Search ................................ 530/300, 327, 530/350; 435/69.1, 7.8, 321

(56) References Cited

U.S. PATENT DOCUMENTS

| | | | |
|---|---|---|---|
| 5,118,792 A | 6/1992 | Warren et al. ............... | 530/350 |
| 5,932,697 A | * 8/1999 | Caceci et al. ................ | 530/350 |

FOREIGN PATENT DOCUMENTS

| | | | | |
|---|---|---|---|---|
| WO | WO-A-90/13571 | 11/1990 | ............ | C07K/7/10 |
| WO | WO 92/16618 | 10/1992 | ........... | C12N/15/00 |

OTHER PUBLICATIONS

Ding, et al., 2000. J Exp Med 191(2):213–223.*
Voet, et al., 1990. Biochemistry, p. 61. John Wiley & Sons, New York.*
Scott, et al., 1987. Eur J. Biochem 168:629–33.*
Hew et al., "Structures of shorthorn sculpin antifreeze polypeptides," *Eur. J. Biochem.* 151, 167–172 (1985), XP–000864304.
Hew et al., "Antifreeze proteins from the shorthorn sculpin, *Myoxocephalus scorpius*: isolation and characterization," Can. J. Biochem 58: 377–383 (1980), XP–000864305.
Wen and Laursen, "Structure–Function Relationships in an Antifreeze Polypeptide," *J. Biol. Chem* 268(22): 16396–16400 (1993), XP–000857648.
Wen and Laursen, "Structure–Function Relationships in an Antifreeze Polypeptide," *J. Biol. Chem.* 267(20): 14102–14108 (1992), XP–002125974.
Chakrabartty et al., "Structure–Function Relationships in a Winter Flounder Antifreeze Polypeptide," *J. Biol. Chem.* 264(19): 11307–11312 (1989), XP–002125975.
Chakrabartty et al., "Structure–Function Relationshp in a Winter Flounder Antifreeze Polypeptide," *J. Biol. Chem.* 264(19): 11313–11316 (1989), XP–002125976.
Wierzbicki et al., "Analysis of Shorthorn Sculpin Antifreeze Protein Stereospecific Binding to (2–10) Faces of Ice," *Biophys. J.* 71: 8–18 (1996), XP–000864303.
Chakrabartty and Hew, The effect of enhanced alpha–helicity on the activity of a winter flounder antifreeze polypeptide, *Eur. J. Biochem.* 202(3): 1057–1063 (1991), XP–002125977.
Greenfield, et al., "Computed Circular Dichroism Spectra for the Evaluation of Protein Conformation," *Biochemistry* 8:4108–4116 (1969).
Ananthanarayan, et al., "Structural Studies on the Freezing–Point–Depressing Protein of the Winter Flounder Pseudopleuronectes Americanus," *Biochem. Biophys. Res. Comm.* 74:685 (1977).
DeVries, "Antifreeze peptides and glycopeptides in cold–water fishes," *Annu. Rev. Physiol.* 45:245–260 (1983).
Pickett, et al., "Sequence of an antifreeze protein precursor," *Eur. J. Biochem.* 143:35–38 (1984).
Scott, et al., "Antifreeze protein genes are tandemly linked and clustered in the genome of the winter flounder," *Proc. Natl. Acad. Sci. USA* 82:2613–2617 (1985).
Kao, et al., "The relationship between molecular weight and antifreeze polypeptide activity in marine fish," *Can. J. Zool.* 64:578–582 (1986).
Scott, et al., "Structural variations in the alanine–rich antifreeze proteins of the pleuronectinae," *Eur. J. Biochem.* 168:629–633 (1987).
Ananthanarayan, et al., "Antifreeze Proteins: Structural diversity and mechanism of action," *Life Chemistry Reports* 7:1–32 (1989).
Chakrabartty, et al., "Structure–Function Relationship in a Winter Flounder Antifreeze Polypeptide," *J. Biol. Chem.* 264:11313–11316 (1989).
Davies, et al., "Biochemistry of fish antifreeze proteins," *FASEB J.* 4:2460–2468 (1990).

(List continued on next page.)

*Primary Examiner*—Jill D. Martin
*Assistant Examiner*—Anne-Marie Baker
(74) *Attorney, Agent, or Firm*—Townsend and Townsend and Crew LLP

(57) ABSTRACT

The present invention provides inter alia, isolated "sculpin-type intracellular AFPs" from shorthorn sculpin and their corresponding nucleic acids. The sculpin-type intracellular AFPs are alanine-rich polypeptides that are synthesized in the peripheral tissues such as the skin and gills of fish. These skin-type AFPs are encoded by a distinct set of AFP genes that lack a signal peptide, which is indicative of their intracellular location. The polypeptides are used to make cells cold resistant and to improve the palatability of cold foods and liquids. Cold resistant eukaryotes and prokaryotes, including plants, animals and bacteria are made using the sculpin-type intracellular antifreeze polypeptides and nucleic acids. Moreover, the present invention provides methods for preserving cells, tissues and organs ex vivo using the AFPs described herein.

22 Claims, 5 Drawing Sheets

OTHER PUBLICATIONS

Lee, J., et al., "The reduction of the freezing point of tobacco plants transformed with the gene encoding for the antifreeze protein from winter flounder," Symposium On Molecular Strategies For Crop Improvement Held At The 19th Annual UCLA (University Of California—Los Angeles) Symposia On Molecular And Cellular Biology, *J. Cell. Biochem. Suppl.* 14 Part E, p. 303 (Abstract) (Apr. 16–22, 1990).

Davies, et al., "Antifreeze protein pseudogenes," *Gene* 112(2):171–178 (1992).

Gong, et al., "Tissue distribution of fish antifreeze protein mRNAs," *Can. J. Zool.* 70:810–814 (1992).

Valerio, et al., "Fish Skin: An effective barrier to ice crystal propagation," *J. Exp. Biol.* 164:135–151 (1992).

Wen, et al., "A model for binding of an antifreeze polypeptide to ice," *Biophys. J.* 63:1659–1662 (1992).

Gong, et al., "Zinc and DNA Binding Properties of a Novel LIM Homeodomain Protein Isl-2," *Biochem.* 33:15149–15158 (1994).

Gong, et al., "Transgenic Fish in Aquaculture and Developmental Biology," *Current Topics in Developmental Biology* 30:178–214 (1995).

Griffith, et al., "Antifreeze proteins and their potential use in frozen foods," *Bioteca Adv.* 13(3):375–402 (1995).

Sicheri, et al., "Ice–binding structure and mechanism of an antifreeze protein from winter flounder," *Nature* 375:427–431 (1995).

Gong, et al., "The antifreeze protein genes of the winter flounder, *Pleuronectus americanus*, are differentially regulated in liver and non–liver tissues," *Biochem. Biophys. Res. Commun.* 206(1):387–392 (1995).

Gong, et al., "Skin antifreeze protein genes of the winter flounder, *Pleuronectes americanus*, encode distinct and active polypeptides without the secretory signal and prosequences," *J. Biol. Chem.* 271(8):4106–4112 (Feb. 23, 1996).

* cited by examiner

```
                    GTGACTCATC AGGAAGTGT TGATCTTTCT CTGTTCCAAA CGCACCGAGC TAAACAAAAG TGAGAATGGC GGCGGCGGCG         80
                                                                                                M   A   A   A   A
  1

K   A   A   E   A   A   A   M   A   A   A   N   A   A   E   A   A   A   T   K   A   A   D   A   A   A   S   A   A   A
  81 AAGGCGGCGG AGGCGGCGCGG AATGGCGGCG GCAAATGCGG CGGAGGCGCGG GGCAACGAAG GCGGCTGATG CGGCTGCGTC GGCGGCAGCT        170

A   A   I   A   A   I   A   E   A   A   E   A   A   A   A   T   K   S   A   N   V   A   A   A   A   A   A
 171 GCGGGCTATTG CGGGCTATTGC GGAGGCGGCG AGGCAGCGCG AACGAAGTCG GCTAATGTAG CGGCGGCGGC GGCAGCGACG        260

S   A   A   A   A   A   K   A   T   A   N   A   A   A   S   A   A   A   A   A   A   V   A   *
 261 TCGGCCGCGG CAGCAGCGAA GGCTACGGCT AATGCGGGCT TCGATATGTG GCAACAAACA TAGTTAATTT GACCTGCGAG GCACTGCGCA CGACCTGCAG GCACAAGTTA CAGCAGTTGC GTAGCAGTGT        350

351 CTCCGTAGAG CAGTTGGCTG CTTATAATGC ATTGTAATAC TTGGATTAT GAATGACAAA AGCAGCATC AGCAGCTGCA GTTCAGTAAT GCACAAGTTA CACTATAAGG        440

441 TTCTTTTAGG GTGTGGGTAG TTGGCTGCTC AGTGTGGTGC TTGTTTATGT CACAGGTTAT ATGGTTTGTC CATGCTTAAT TCTTAATCCC        530

531 TGATGTTGCT GACCCAACTC AGTGTGGTGC TGCTGAATAT CACAGGTTAT TAATACGTAA ATTCAAGTAT GGAACACACA        620

621 TGTTATTTG TTGTTGTGAA AAACACATTC AATCAAACAA TAACCAAGAA AGTGAACCT CAGTATAATC AATTTAAATG        710

711 TGTGGTTAAA AACTCACTGC GTAGCTTAAA GATCTCATCA GTGTTGATGA GCAAAGTCGT CCACAAAGAT CTTTCTTTAG        800

801 AGCTAATGTA GTAGCTTAAA GATCTCATCA GTGTTGATGA GCAAAGTCGT TGGTGAACAA ACTGTACCTC TTTAAAAACG TTTTGAAGTT        890

891 CAGACCGGAG CTAAAACTCC CATTTATCTC AAAAAAAAAA AAAAAAAAAA        980

981 TAAACAAAAA AAAAAAAAAAA AAAAAAA        1027
```

FIG. 1.

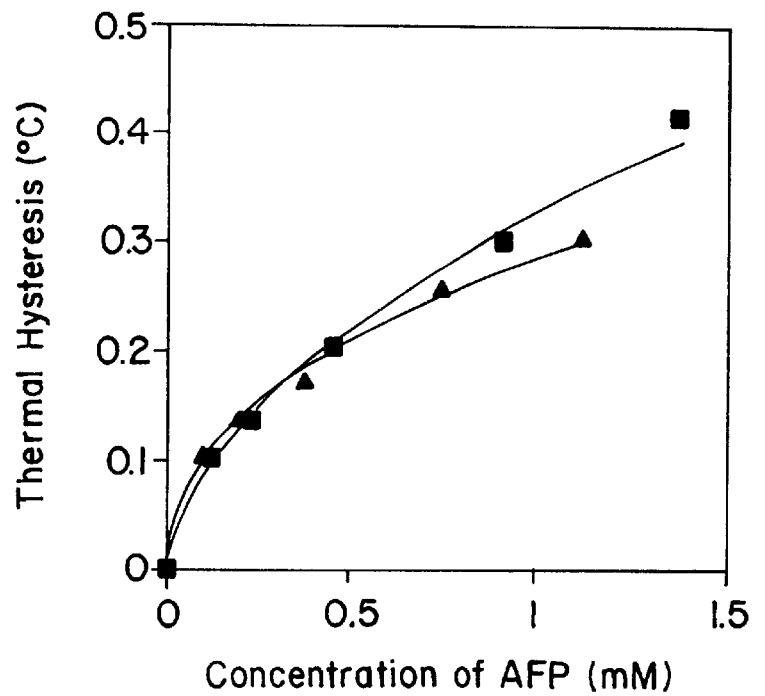
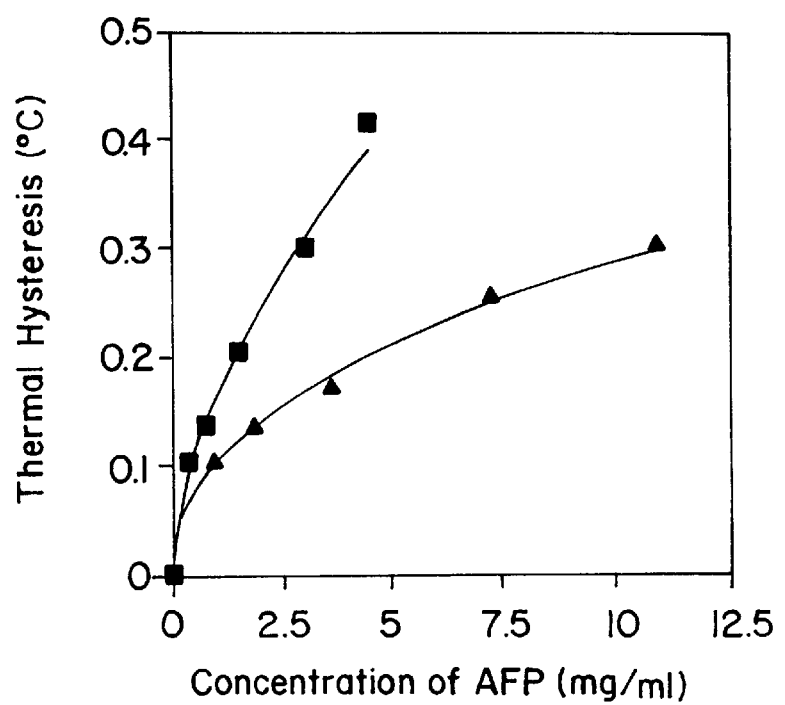
FIG. 2.

SEQ ID NO:4 wfl AFP-6  DTASDA AAAAL TAAN AKAAAEL TAAN AAA AAAAT AR

SEQ ID NO:5 wfs AFP-1  MDAP AR AAAA TAAA AKAAAE AT K AAAA K AAAAT KAAAH

FIG. 4.

```
                    AFP1
             wfs                                                                    wf1
                                                                                    AFP-6
                  AC TGT CGA CCA GCA CTC AGA ATC ACT GAC ATC AAC ATG GAC GCA CCA GCC    47
              1   AGA GCC GCA GCC ACC GCC AAG GCC GCC GCT GCC AAA GCC GCA GAA GCC      95
             48   ACC AAA GCC TGA TGA GCC TGG TCG TCT TGA TGT GGG ATC ATG TGA ACA TCT GAG  143
             96   CAT TAA CGA GAT GTT ACC AAT CTG CTG AAT AAA CCT GAG AAG CTG TTT GTT  191
SEQ ID NO.:6  144  CAG CGA GA                                                          239
             192                                                                        241
             240  GA 1   ACCACATCTT CATTTTGTAG TGAACCAGTG CTCCCCTACAA GTTCTCAAAA TGGCTCTCTC    60
             61   ACTTTTCACT GTCGGACAAT TGATTTTCTT ATTTTGGACA ATGAGAATCA CTGAAGCCAG   120
SEQ ID NO.:7 121  CCCCGACCCC GCAGCCAAAG CCGCCCCAGC AGCAGCTGCC GCCCCTGCCG CAGCCGCCCC   180
             181  AGACACCGCC TCTGACGCCG CCGCTGCAGC CGCCCTTACC GCCGCCAATG CCGCCGCCGC   240
             241  CGCCAAACTC ACCGCCGACA ACGCCGCCGC CGCCGCAGCA GCCACCCGCCA GAGGTTAAGG   301
             301  ATCGTGGTCG TCTTGATGTG GG                                              322

AFP8
             wfs
                  TT CAC TGT CGA ACA CTC AGA ATC ACT GAC ATC AAC ATG GAC GCA CCA     47
              1   GCC GCC ACC GCC GCA GCT GCC ACC GCC GCC GCC AAG GCC ACT GCC GAA     95
             48   GCC ACC GCC AAA GCA GCC ACC GCA GCC GCA GCC GCA GCC GCC GCC        143
             96   GCC GCC CGT TAA GGA TCA TCG TCT TGC TGT GGG ATC ATG TGA ACA TCT    191
SEQ ID NO.:8 144  GCC GAG CAG CGA GAT GTC ACC AAT CTG TTG AAT AAA GCT GAG AAG CTG TTT   239
             192  GTT TA                                                                287
             240                                                                        292
             288

FIG. 5.
```

SCULPIN-TYPE ANTIFREEZE POLYPEPTIDES AND NUCLEIC ACIDS

CROSS-REFERENCES TO RELATED APPLICATIONS

This application claims priority to U.S. Provisional Application Ser. No. 60/090,794, filed Jun. 26, 1998 and No. 60/095,713, filed Aug. 7, 1998, the teachings of which are incorporated herein by reference in their entirety for all purposes.

BACKGROUND OF THE INVENTION

The survival of cellular organisms is dependent on the physical properties of water. The freezing point of liquid water sets the lower limit for the survival of most cells, because the formation of ice causes dehydration and osmotic damage to the cell. Organisms that inhabit sub-zero environments, have special adaptations which permit the organism to survive. For example, Arctic and Antarctic fish which live in cold seawater have various macromolecular antifreeze polypeptides in the serum of their blood. Such antifreeze polypeptides are a mixture of glycoproteins having a range in relative molecular mass ($M_r$) from about 2,500 to 34,000 (antifreeze glycoproteins, or "AFGPs") and antifreeze polypeptides (AFPs) with $M_r$ from about 3,300 to 12,000. Ananthanarayanan (1989) *Life Chemistry Reports* 7:1–32 provides an overview of AFPs and AFGPs. See also DeVries (1983) *Annu. Rev. Physiol* 45: 245–260; Davies et al., (1990) *FASEB J* 4: 2460–2468 and Warren et al., U.S. Pat. No. 5,118,792.

At present, four distinct types of AFPs have been characterized from a variety of cold water fish See, Davies et al., (1990) *FASEB J*. 4: 2460–2468; and Griffith and Ewart et al. (1995) *Bioteca Adv.* 13(3): 375–402, and references therein. Type I AFPs are alanine-rich, α-helical polypeptides, found in many right-eye flounders and sculpins. Type II AFPs are enriched with cysteine and are found in sea raven, smelt and herring. Type III AFPs are globular proteins found in several Zoarcoid families including eelpout and wolffish. Type IV AFPs are characterized by a helix bundle and have been found in longhorn sculpin, *Myoxocephalus octodecimspinosis* (see, G. Deng et. al. (1997) *FEBS Letters* 402: 17–20. Although the different AFPs and AFGPs are structurally distinct, they share the ability to inhibit ice crystal growth by binding to the ice surface.

AFPs in the liver (liver-type AFPs; Type I) from the Winter flounder, *Pleuronectus americanus*, have been studied extensively in terms of their structure and function, gene organization, gene expression and regulation. The genome of the Winter flounder contains multiple copies of liver or serum type AFP genes, most of which are arranged as regular tandem repeats (Scott et al., (1985) *Proc. Natl. Acad Sci. USA*. 82: 2613–2617).

WO97/28260 describes the presence of new isoforms of AFPs in the Winter flounder, *Pleuronectes americanus* that are synthesized in the peripheral tissues, such as the skin and gills. These AFPs are referred to as "skin-type AFPs" and are encoded by a distinct set of AFP genes that lack a signal peptide which is indicative of their intracellular location. Examples of skin isotypes from the Winter Flounder are wfsAFP-1 and wfsAFP-8. The presence of extracellular and intracellular AFPs with differential tissue expression within a single fish species has raised questions about the relative roles of these AFP isoforms in cold protection, function, and evolutionary relationship.

There exists a need in the art for new AFPs with unique physiologic function and in situ location that inhibit ice recrystallization and induce a concentration-dependent decrease in the freezing point of aqueous solutions. The present invention fulfills these and other needs.

SUMMARY OF THE INVENTION

The present invention relates to a new intracellular AFP found in the shorthorn sculpin (*Myoxocephalus scorpius*) ("sculpin-type AFP"). These new sculpin-type AFPs aid the fish in its defense against the dangers of freezing in the ice-laden, sub-zero sea water. The shorthorn sculpin synthesizes AFPs that serve to depress the freezing temperature of its intracellular fluids. These sculpin-type AFPs thus function as protectors of intracellular components.

As such, the sculpin-type AFPs of the invention are generally useful in protecting solutions against freezing. This improves the shelf-life of many refrigerated foods, making the foods more palatable. The sculpin-type AFP, when added, inhibits ice recrystallization during cold storage, improving the texture and palatability of the food. In addition, cells that express the sculpin-type AFPs of the invention are more cold-tolerant than counterpart cells which do not express sculpin-type AFPs. Thus, the sculpin-type AFPs of the invention are used to improve the cold tolerance of bacteria, cell cultures, plants and animals. The sculpin-type AFPs of this invention can also be expressed in commercially farmed fish such as catfish, Atlantic salmon and talipia to improve the freeze tolerance of the fish. Sculpin-type AFPs also have certain antibacterial properties, providing a means of reducing unwanted bacteria in foods such as recombinant fruits expressing sculpin-type AFPs, and in blended food stuffs such as ice cream. This improves shelf life, food quality, and makes such products safer for consumption. These and other commercial applications are aspects of the present invention.

In one aspect, the present invention relates to an isolated intracellular antifreeze polypeptide (sculpin-type AFPs). In this embodiment, the polypeptide typically comprises four or more $Pr-X_2-Pr-X_7$ subsequences, where Pr is a polar amino acid and X is a naturally occurring or synthetic amino acid. The polypeptide is alanine rich, with X being predominately alanine. The sculpin-type AFPs of the present invention have the physical ability to induce a concentration-dependent decrease in the freezing point of an aqueous solution such as water.

The polypeptide typically comprises at least six of these 11 amino acid subsequences (note that the subsequences are overlapping) where the polar amino acids are N, D, E, and K. In addition, the preferred polypeptides have a MW of about 7900 DA to about 9700 DA. Typically, the sculpin-type AFPs are between about 45 and about 100 amino acids in length, more preferably between about 60 and 100 amino acids in length, and most preferably about 80–100 amino acids in length.

Preferred sculpin-type AFPs of the present invention are optionally assessed by examining the secondary structure of the polypeptides. In certain aspects, the polypeptides of the present invention, as measured by circular dichroism, are at least 70% α-helical and, preferably at 0° C., essentially entirely α-helical. Certain polypeptides of the invention optionally do not meet these criteria, e.g., where the polypeptide is a fusion protein that includes subsequences that are unrelated to a sculpin-type AFP. Fusion proteins comprising sculpin-type AFP subsequences are a feature of the present invention.

Sculpin-type AFPs of the present invention are optionally defined by their immunological characteristics. Preferred sculpin-type AFPs bind polyclonal antibodies raised against the polypeptide shorthorn sculpin skin-type (sssAFP-2; SEQ ID NO:2). Preferred polypeptides also bind to polyclonal antibodies raised against the polypeptide sssAFP-2, where the polyclonal antisera are first subtracted with a skin-type polypeptide, such as wfsAFP-1, from the Winter Flounder.

In certain embodiments, polyclonal antisera for use in immunoassays are generated using sssAFP-2 as described herein. The polyclonal antisera is then tested for its cross-reactivity against skin-type AFPs from Winter flounder (e.g. wfsAFP-1 i.e., a skin isotype from the Winter flounder) using a competitive binding immunoassay. For example, the immunogenic polypeptide is immobilized to a solid support. wfsAFP-1 added to the assay competes with the binding of the antisera to the immobilized antigen. The ability of the skin-type AFPs from Winter flounder (wfsAFP-1) to compete for binding of the antisera to the immobilized protein is compared to the immunogenic polypeptide. The percent cross-reactivity for the above proteins is calculated, using standard calculations. Those antisera with less than 10% cross-reactivity with skin-type wfsAFP- 1 are selected and pooled. The cross-reacting antibodies are then removed from the pooled antisera by immuno absorbtion (subtraction) with wfsAFP-1. Preferred polypeptides are those that bind to the antisera raised against sssAFP-2 that has been subtracted with wfsAFP-1.

The isolated polypeptides are optionally present as purified lyophilized powders in aqueous solutions (e.g., comprising water, for instance with salts at physiological concentrations), in recombinant cells, plants, animals, bacteria, prokaryotes, cell extracts and the like. The polypeptides are optionally present in foods such as ice cream or frozen yogurt.

The isolated antifreeze polypeptides are optionally encoded by a coding nucleic acid (RNA or DNA) which hybridizes to a skin-type antifreeze nucleic acid encoding sssAFP-2 under high-stringency wash conditions. Preferably, the sculpin-type AFPs do not hybridize significantly to skin-type AFPs from Winter flounder under the same high-stringency wash conditions. In this aspect, the skin-type AFPs from Winter flounder do not significantly hybridize to a nucleic acid of the present invention, where the signal-to-noise ratio on a Southern or northern blot is reduced 75% or more, as compared to the binding of a fully complementary sculpin-type AFP. For example, if a radiolabeled nucleic acid probe from skin-type Winter flounder and a radiolabeled skin-type probe of this invention with the same specific activity are allowed to hybridize to duplicate Southern blots and an autoradiogram shows that the signal from the Winter flounder-specific probe has less than 25% the intensity of the skin-specific probe of this invention after a high-stringency wash, then the nucleic acid detected is a skin specific nucleic acid of this invention.

The present invention also provides nucleic acids such as expression vectors that encode sculpin-type AFPs. The sculpin-type AFPs encoded in the expression vector typically have the same properties as the isolated polypeptides described above and herein. Preferably, the expression vector encodes a skin-type intracellular antifreeze nucleic acid that hybridizes to a second skin-type, antifreeze sssAFP-2 nucleic acid in a Southern or northern blot under high-stringency conditions, but does not significantly hybridize to the nucleic acid wfsAFP- 1 from Winter flounder (skin isotype from the Winter flounder) under the same conditions. The skin-type intracellular antifreeze nucleic acid encodes a skin-type antifreeze polypeptide with the properties described above and herein. For example, the expression vector can encode a nucleic acid coding for polypeptide of SEQ ID NO:2.

The invention provides recombinant cells having a skin-type antifreeze nucleic acid that encodes a skin-type antifreeze polypeptide with the properties discussed above and herein. These cells typically express the sculpin-type AFP, but in certain embodiments, such as cells used in cloning, the cell does not necessarily express a sculpin-type AFP. Additionally, the nucleic acids are optionally linked to promoters active only under selected conditions. Cells expressing the polypeptide are cold resistant, meaning they can tolerate colder temperatures than similar cells which do not express a sculpin-type AFP, and can more readily survive freezing. The cell is optionally a eukaryotic cell such as a plant, fungal or animal cell, or is optionally a prokaryotic cell such as a bacterium, or is optionally an archaebacterial cell. It should be appreciated that cold tolerance is especially important in agriculture, aquaculture and food processing. Accordingly, cells for such applications are preferably transduced with sssAFP-2 nucleic acids as noted herein.

In still yet another aspect, the present invention relates to methods of depressing the freezing point of an aqueous composition by adding sculpin-type AFPs to the aqueous composition. Preferred sculpin-type AFPs of the invention depress the freezing point of an aqueous solution in a concentration-dependent manner. Additional methods of this invention relate to the inhibiting of ice recrystallization in certain compositions, especially foods such as diary products. The present invention also provides stabilization of certain biological and synthetic membranes using sculpin-type AFPs of this invention. In another embodiment, the present invention provides method for preserving cells, tissues and organs ex vivo using the sculpin-type AFPs, preferably, sssAFP-2.

In certain other aspects, the present invention provides antibodies that specifically bind to a skin-type antifreeze polypeptides herein. Preferred antibodies are specific for sssAFP-2. Indeed in one class of embodiments, the sculpin-type AFPs of the invention are optionally identified by binding to an antibody specific for a selected sculpin-type AFP. In addition to use in western blotting and immunoassay methods, a repeatable method of pooling antibodies is used for peptide identification.

In this aspect, an isolated intracellular antifreeze polypeptide where the polypeptide is selected based upon binding to a pool of subtracted polyclonal antibodies, where the original polyclonal antibodies are raised against the sssAFP-2 polypeptide from shorthorn sculpin and then subtracted with a different AFP such as wfsAFP- 1, from Winter flounder as previously described.

In other aspects, the present invention relates to an isolated nucleic acid encoding the isolated, intracellular antifreeze polypeptides described above and herein. Nucleic acids include s3-2 and s17-12.

BRIEF DESCRIPTION OF THE DRAWINGS

FIG. 1 illustrates the sequence of clone s3-2 that encodes a 92-residue shorthorn sculpin skin-type AFP (sssAFP-2) (SEQ. ID NO:2). The ORF begins at the ATG start signal at position 66 and ends at the stop codon TAG at position 342 indicated by the asterisk. The complete cDNA clone is approximately 1.1 kb. See, also SEQ ID NO: 1

FIGS. 2A and 2B illustrate the thermal hysteretic activity of His-sssAFP-2 and wflAFP-6, measured in molar concentration (A), and in mg/mL (B).

FIG. 4 illustrates the amino acid sequences of representative antifreeze polypeptides. wflAFP-6 refers to a specific Winter flounder liver type antifreeze polypeptide with the amino acid sequence of SEQ ID NO:4. wfsAFP-1 refers to a specific Winter Flounder skin-type antifreeze polypeptide with the amino acid sequence of SEQ ID NO:5.

FIG. 5 illustrates the nucleic acid sequences corresponding to wfsAFP-1, wflAFP-6 and wfsAFP-8 from Winter flounder having SEQ ID NO:6, SEQ ID NO:7 and SEQ ID NO:8, respectively.

DEFINITIONS

Figure 3:
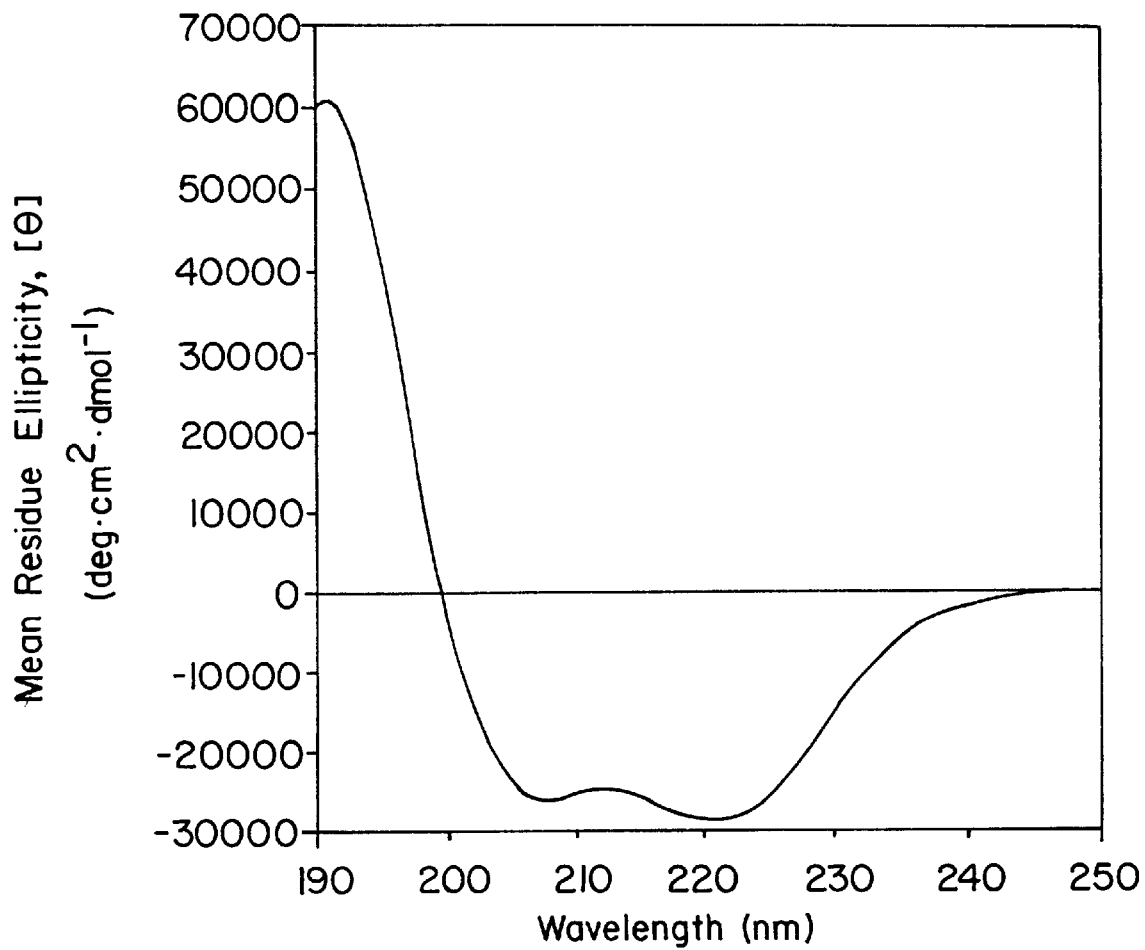
FIG. 3 illustrates a circular dichroic spectrum of His-sssAFP-2. The spectrum is the average of four measurements at 0° C. with His-sssAFP-2 concentrations of ~0.1 mg/mL. From the molar ellipticity at 222 nm, the α-helical content of His-sssAFP-2 was calculated to be approximately 74%.

The term "antibody" refers to a polypeptide substantially encoded by an immunoglobulin gene or immunoglobulin genes, or fragments thereof The recognized immunoglobulin genes include the kappa, lambda, alpha, gamma, delta, epsilon and mu constant-region genes, as well as the immunoglobulin variable-region genes. Light chains are classified as either kappa or lambda. Heavy chains are classified as alpha, gamma, delta, epsilon and mu, which in turn define the immunoglobulin classes, IgA, IgG, IgD IgE and IgM, respectively. An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light-chain ($V_L$) and variable heavy-chain ($V_H$) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, Third Edition, W. E. Paul, ed., Raven Press, NY (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

The terms "isolated" or "biologically pure" refer to material that is substantially or essentially free from components that normally accompany the material as found in its naturally occurring environment. The isolated material optionally comprises material not found with the material in its natural environment. For instance, "isolated" sculpin-type AFPs naturally found in fish optionally include heterologous cell components, food materials and the like.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof A nucleic acid "encodes" another nucleic acid where it is the same as the specified nucleic acid, or complementary to the specified nucleic acid. A coding nucleic acid is a nucleic acid which encodes a polypeptide and which can be transcribed, translated and/or expressed by a cell. Unless indicated to the contrary, the coding nucleic acid can be either a sense or antisense nucleic acid e.g., an mRNA, or either strand of a cDNA.

The term "operably linked" refers to a functional linkage between the expression control sequence of a nucleic acid (such as a promoter or an array of transcription factor binding sites) and a second nucleic acid sequence, wherein the expression-control sequence directs transcription of the nucleic acid corresponding to the second sequence.

An "expression vector" includes a recombinant-expression cassette that includes a nucleic acid encoding a polypeptide that can be transcribed, translated and expressed by a cell. A "recombinant-expression cassette" is a nucleic acid construct, generated recombinantly or synthetically, with a series of nucleic acid elements that permit transcription of a particular nucleic acid in a target cell and, typically, translation of the expressed nucleic acid. The expression vector can be, e.g., a plasmid, virus, or nucleic-acid fragment thereof Typically, the recombinant expression cassette portion of the expression vector includes a nucleic acid to be transcribed, and a promoter. In some embodiments, the expression cassette also includes, e.g., an origin of replication and/or chromosome integration elements. A "promoter" is an array of nucleic-acid control sequences that direct transcription of a nucleic acid in a cellular environment. As used herein, a promoter includes necessary nucleic acid sequences near the start site of transcription, such as, in the case of a polymerase II type promoter, a TATA element. The promoter also optionally includes distal enhancer or repressor elements that can be located as much as several thousand base pairs from the start site of transcription. A "constitutive" promoter is a promoter that is active under most environmental conditions and states of development or cell differentiation. An "inducible" promoter responds to an extracellular stimulus.

The term "recombinant", when used with reference to a cell, indicates that the cell replicates or expresses a nucleic acid, or expresses a peptide, protein or fragment thereof, encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The term "recombinant", when used with reference to a nucleic acid refers to two or more fragments of nucleic acid ligated in a continuous sequence which are not normally found in nature together in the same sequence. For example, a fragment of the gene to be cloned inserted into a vector to produce a recombinant nucleic acid.

The term "heterologous" when used with reference to a nucleic acid indicates that the nucleic acid comprises two or more subsequences that are not found in the same relationship to each other in nature. For example, the nucleic acid is typically recombinantly produced, having two or more sequences from unrelated genes arranged to make a new functional nucleic acid. For instance, a first nucleic acid has a promoter from one gene arranged to direct the expression of a coding sequence from a second gene.

The term "subsequence" in the context of a particular nucleic acid or polypeptide sequence refers to a region of the nucleic acid or polypeptide equal to or smaller than the particular nucleic acid or polypeptide. Certain polypeptides of the invention optionally include multiple domains derived from more than one polypeptide. For example, fusion proteins comprising sculpin-type AFP subsequences are a feature of the invention. Preferred fusion proteins include a sculpin-type AFP subsequence (typically at least 30%, generally 50%, often 70%, preferably about 80%, occasionally 90%, most preferably 100% of a given sculpin-type AFP), and subsequences from a common fusion moiety useful for modifying the immunogenicity or facilitating purification of the fusion protein.

The terms "stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* Part I; Chapter 2 "Overview of Principles of Hybridization and the Strategy of Nucleic Acid Probe Assays", Elsevier, NY Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0. 15M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example of a medium stringency wash for a duplex of more than 100 nucleotides, is 1×SSC at 45° C. for 15 minutes. An example of low stringency wash for a duplex of more than 100 nucleotides, is 4–6×SSC at 40° C. for 15 minutes. In general, a signal-to-noise ratio at least 2×greater than that observed for an unrelated probe in the particular hybridization assay indicates detection of a specific hybridization. More preferably, a signal-to-noise ratio at least 5×–10× greater than that observed for an unrelated probe in the particular hybridization assay indicates detection of a specific hybridization. Even more preferably, a signal-to-noise ratio at least 5×–10×greater than that observed for an unrelated probe in the particular hybridization assay indicates detection of a specific hybridization.

Preferably, the sculpin-type antifreeze polypeptides of the present invention do not hybridize significantly to AFPs from Winter flounder under the same high-stringency wash conditions. In this aspect, the skin-type AFPs from Winter flounder do not significantly hybridize to a sculpin-type nucleic acid of the present invention, if the signal-to-noise ratio on a Southern or northern blot is reduced 75% or more, 65% or more, or even 50% or more, as compared to the binding of a fully complementary sculpin-type AFP.

Nucleic acids that do not hybridize to each other under stringent conditions are still substantially identical if the polypeptides that they encode are substantially identical. This occurs when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity can be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

Methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol Biol.* 48: 443; by the search for similarity method of Pearson and Lipman (1988) *Proc. Natl. Acad Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 *Science* Dr., Madison, Wis., USA); the CLUSTAL program is well described by Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the BioSciences* 8, 155–65, and Pearson, et al. (1994) *Methods in Molecular Biology* 24, 307–31. Alignment is also often performed by inspection and manual alignment.

One example of a useful alignment algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences.

This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. A preferred sculpin-type AFP of the present invention is at least 70%, more preferably 80%, still more preferably 90%, and most preferably 95% or more identical to sssAFP-2 using PILEUP with defined parameters.

Another example of algorithm that is suitable for determining percent sequence identity and sequence similarity is the BLAST algorithm, which is described in Altschul et al. *J. Mol. Biol.* 215:403–410 (1990). Software for performing BLAST analyses is publicly available through the National Center for Biotechnology Information (http://www.ncbi.nlm.nih.gov/). This algorithm involves first identifying high-scoring sequence pairs (HSPs) by identifying short words of length W in the query sequence, which either match or satisfy some positive-valued, threshold score T when aligned with a word of the same length in a database sequence. T is referred to as the neighborhood word-score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001 or more identical to sssAFP-2 using PILEUP with defined parameters.

A further indication that two nucleic acid sequences or polypeptides are substantially identical is that the polypeptide encoded by the first nucleic acid is immunologically cross reactive with the polypeptide encoded by the second nucleic acid, as described herein. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

The phrase "conservatively modified variations" of a particular nucleic acid sequence refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of "conservatively modified variations." Every nucleic acid sequence herein that encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each "silent variation" of a nucleic acid that encodes a polypeptide is implicit in each described sequence. Furthermore, one of skill will recognize that individual substitutions, deletions or additions which alter, add or delete a single amino acid or a small percentage of amino acids in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See, Creighton (1984) "Proteins," W.H. Freeman and Company.

The term "amino acid" refers to the naturally occurring α-amino acids and/or synthetic amino acid mimetics. The term includes both D- and L-amino acids. This group includes, but is not limited to, glycine; alanine; valine; leucine; isoleucine; serine; phenylalanine; tryptophan; proline; hydroxy proline; methionine; aspartate; asparagine; glutamic acid; glutamine; lysine; arginine; histidine; threonine; tyrosine and cysteine.

The term "polar amino acid" refers to amino acids which possess side chains that preferentially dissolve in polar solvents. These amino acids tend to be hydrophilic in nature. Relative polarity can be measured by distributing an amino acid between a nonpolar solvent, such as dioxane, and a polar solvent such as water. Polar amino acids will distribute preferably in the water layer. Polar amino acids include, but are not limited to, arginine, asparagine, aspartic acid, cysteine, glutamine, glutamic acid, lysine, proline and serine.

The term "Pr-$X_2$-Pr-$X_7$" refers to an eleven amino acid subsequence or motif present in the sculpin-type AFPs of this invention. Each Pr, which can be the same or different, is a polar amino acid as defined above. Each X is independently an amino acid as defined above. In some embodiments, the eleven amino acid subsequences can overlap. For instance, with reference to FIG. 1, the second 11 amino acid subsequence has the sequence NAAEAAAT-KAA (SEQ ID NO:9). Residues 9–11 are KAA. The third subsequence has the amino acid sequence KAADAAASAAA (SEQ ID NO:10). Residues 1–3 are KAA. In this manner, the second subsequence and the third subsequence overlap.

The term "sssAFP-2" refers to a specific shorthorn sculpin skin-type antifreeze polypeptide with the amino acid sequence of SEQ ID NO:2.

The term "wflAFP-6" refers to a specific Winter flounder liver type antifreeze polypeptide with the amino acid sequence of SEQ ID NO:4.

The term "wfsAFP-1" refers to a specific Winter flounder skin-type antifreeze polypeptide with the amino acid sequence of SEQ ID NO:5.

The term "s3-2" refers to a 1027 base-pair cDNA clone (SEQ ID NO: 1) encoding the antifreeze polypeptide sssAFP-2 with the amino acid sequence of SEQ ID NO:2.

The term "s17-12" refers to a 991 base-pair cDNA clone (SEQ ID NO:3) encoding the antifreeze polypeptide with the amino acid sequence of SEQ ID NO:2.

The term "His-sssAFP-2" refers to the recombinant protein expressed when the 276 bp ORF of s3-2 was cloned into an expression vector. The recombinant protein contained a 20-residue histidine-tag with a single thrombin cleavage site at the N-terminus of the full 92-amino acid residue sequence.

The phrase "concentration dependent decrease in freezing point of an aqueous solution" refers to the effect of decreasing the temperature at which an aqueous solution solidifies with increasing concentration or amount of sculpin-type AFPs. The preferred method of measuring the effect of a sculpin-type AFP on the freezing point of an aqueous solution is to measure the thermal hysteresis (the difference between the melting and freezing temperatures). This can be done by performing a serial dilution of the sculpin-type AFP-containing aqueous solution, followed by cooling the solution gradually and monitoring the freezing point of the solution. Typically, this is performed using commercially available equipment designed specifically for this purpose, such as nanoliter osmometry.

The phrase "sculpin-type AFP" is an antifreeze protein, found, for example, in the skin of shorthorn sculpin. In general, several types of AFPs found in various tissues and organs, have been characterized from a variety of cold water fish. Type I AFPs are alanine-rich, α-helical polypeptides, found in many right-eye flounders and sculpins. Type II AFPs are enriched with cysteine and are found in sea raven, smelt and herring. Type III AFPs are globular proteins found in several Zoarcoid families including eelpout and wolffish. Type IV AFPs are characterized by a helix bundle and have been found in longhorn sculpin, Myoxocephalus octodecimspinosis. The intracellular sculpin-type AFPs of this invention are Type I AFPs that are alanine-rich polypeptides that are synthesized in the peripheral tissues such as the skin and gills of fish. These sculpin-type AFPs are encoded by a distinct set of AFP genes that lack a signal peptide, which is indicative of an intracellular location. The sculpin-type AFPs share common epitopes which are recognized by antibodies, and share the common ability to inhibit the formation of ice crystals, thereby depressing the freezing point of aqueous solutions.

Sculpin-type promoters are promoters that direct expression of a nucleic acid in the skin of a shorthorn sculpin. The promoter also typically directs lower levels of expression of the nucleic acid in tissues other than the skin. The promoter is optionally heterologous, i.e., the promoter is optionally used to direct expression of nucleic acids unrelated to sculpin-type AFPs, e.g., where high levels of expression of a nucleic acid in the skin are desirable. The promoter is optionally used as part of an AFP gene, where it is typically in its naturally occurring relationship with the AFP coding sequence.

The term "wild type" refers to the normal genotype and/or phenotype of a particular cell as found in nature.

The term "α-helical" refers to the secondary structure of a polypeptide, protein or fragment thereof The α-helix is characterized as a rod-like structure, wherein the tightly coiled main chain of the polypeptide forms the inner part of the rod and the side chains extend outward in a helical array. There is about a 1.5 Å rise and about 100-degree rotation as measured between adjacent α-carbon atoms in an α-helical structure. The percent α-helix of a peptide or protein can be measured using circular dichroism, x-ray diffraction, or other methods well known to those of skill in the art. The term α-helix is well known to those of skill in art. This definition is provided to supplement, but not replace other meanings of the term.

The term "thrombin cleavage site at the N-terminus" refers to a subsequence of amino acids, which is recognized by the enzyme thrombin and can be cleaved by the peptidase activity of the thrombin. The site is located at the N-terminus, which refers to the end of the peptide or protein wherein the final amino acid residue is joined to the rest of the molecule via a peptide bond with the carboxylic acid portion of the residue, leaving the amino group free.

The term "decrease in ice recrystallization" refers to the ability of sculpin-type AFPs to retard or inhibit the formation of ice crystals in solutions containing sculpin-type AFPs.

The term "stabilizes a membrane" refers to the ability of sculpin-type AFPs to protect membranes during cooling, thereby preventing or inhibiting the loss of the membrane contents or the prevention of loss of membrane function. For instance, when liposomes are cooled to low temperatures, their membranes become leaky, resulting in the loss of intracellular contents. The sculpin-type AFPs of this invention, stabilize the membrane and reduce or inhibit the loss of the contents.

DETAILED DISCUSSION OF THE INVENTION

A. Introduction

The present invention provides, inter alia, isolated intracellular "sculpin-type AFPs" e.g., from shorthorn sculpin, and their corresponding nucleic acids. The intracellular sculpin-type AFPs are alanine-rich polypeptides that are synthesized in the peripheral tissues, such as the skin and gills of fish. These sculpin-type AFPs are encoded by a distinct set of AFP genes that lack a signal peptide, which is indicative of their intracellular location.

As discussed fully herein, a cDNA clone that encodes an antifreeze protein was isolated from a skin library from shorthorn sculpin. The clone encodes a mature, 92-residue mature polypeptide (SEQ ID NO:2) without any signal or prosequence, which confirms an intracellular localization. It is the largest alanine-rich, α-helical Type I antifreeze protein known. In addition, a recombinant fusion protein containing an N-terminal linked His-tag was produced and purified from E. coli. This recombinant fusion protein is α-helical at 0° C. and exhibits significant antifreeze activity. Northern blot and reverse transcriptase-PCR analyses indicates that sssAFP-2 mRNA is present in peripheral tissues such as skin and dorsal fin, but is absent in the liver. These results indicates that the external tissues of cold-water marine fish are major organs for antifreeze protein synthesis and are likely the first line of defense against the threat of freezing.

B. Intracellular Sculpin-type AFPs

In one embodiment, the present invention relates to an isolated skin-type intracellular antifreeze polypeptide comprising four or more $Pr-X_2-Pr-X_7$ subsequences. In this subsequence, Pr is a polar amino acid and X is a member independently selected from the group of natural and synthetic amino acids. The sculpin-type AFPs of this invention induce a concentration-dependent decrease in the freezing point of aqueous solutions.

In some embodiments, the 11-amino acid subsequences can optionally overlap. For instance, with reference to FIG. 1, the second 11-amino acid subsequence has the sequence NAAEAAATKAA (SEQ ID NO:9). Residues 9–11 are KAA. The third subsequence has the amino acid sequence KAADAAASAAA (SEQ ID NO:10). Residues 1–3 are KAA. In this manner, the second subsequence and the third subsequence overlap. In a preferred embodiment of the present invention, the subsequences can overlap between about 1 and about 5 residues, and more preferably between about 1 and about 3 residues.

In preferred embodiments, the sculpin-type AFPs of this invention comprise at least five $Pr-X_2-Pr-X_7$ subsequences, and more preferably, at least six $Pr-X_2-Pr-X_7$ subsequences. In certain aspects, sculpin-type AFPs of this invention are alanine-rich, amphipathic, α-helical peptides, wherein the hydrophilic polar residues (Pr) are preferably amino acids independently selected from the group of N, D, E, and K. X is preferably a natural amino acid independently selected from the group of A, S, V, E, T, M and K. In addition, the preferred polypeptides have a MW of about 7900 DA to about 9700 DA. Typically, the sculpin-type AFPs are between about 45 and about 100 amino acids in length, more preferably between about 60 and 100 amino acids in length, and most preferably about 80–100 amino acids in length.

In a preferred aspect, the sculpin-type AFP of the present invention is sssAFP-2 (SEQ ID NO:2). With reference to FIG. 1, the 11-residue repeats are indicated by the boxed residues. The alanine content of sssAFP-2 is approximately 70 %, and at physiological temperature, the secondary structure of sssAFP-2 is almost entirely helical at 37° C.

C. Making Sculpin-type AFP Nucleic Acids and Polypeptides

Several specific nucleic acids encoding sculpin-type AFPs are described herein. These nucleic acids can be made using standard recombinant or synthetic techniques. Given the nucleic acids of the present invention, one of skill can construct a variety of clones containing functionally equivalent nucleic acids, such as nucleic acids that encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found, for example, in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Aldrich Chemical Company (Milwaukee, Wis.), GIBCO BRL Life Technologies, Inc. (Gaithersberg, Md.), Fluka Chemica-Biochemika Analytika (Fluka Chemie A G, Buchs, Switzerland), Invitrogen, (San Diego, Calif.), and Applied Biosystems (Foster City, Calif.), as well as many other commercial sources known to one of skill.

The sculpin-type AFP nucleic acid compositions of this invention, whether RNA, cDNA, genomic DNA, or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro techniques suitable for amplifying sculpin-type AFP nucleic acid sequences for use as molecular probes or generating nucleic acid fragments for subsequent subcloning are available. Examples of techniques sufficient to direct persons of skill through in vitro amplification methods, including the polymerase chain reaction (PCR) the ligase chain reaction (LCR), Qβ-replicase amplification and other RNA polymerase-mediated techniques (e.g., NASBA) are found in Berger, Sambrook et al. (1989) *Molecular Cloning—A Laboratory Manual* (2nd Ed) Vol. 1–3; and Ausubel, as well as Mullis et al., (1987) U.S. Pat. No. 4,683,202; PCR Protocols *A Guide to Methods and Applications* (Innis et al. eds) Academic Press Inc. San Diego, Calif. (1990) (Innis); Arnheim & Levinson (Oct. 1, 1990) C&EN 36–47; The Journal Of NIH Research (1991) 3, 81–94; (Kwoh et al. (1989) *Proc. Natl. Acad Sci. USA* 86, 1173; Guatelli et al. (1990) *Proc. Natl. Acad Sci. USA* 87, 1874; Lomell et al. (1989) *J. Clin. Chem* 35, 1826; Landegren et al. (1988) *Science* 241, 1077–1080; Van Brunt (1990) *Biotechnology* 8, 291–294; Wu and Wallace, (1989) Gene 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. All of these in vitro amplification methods are suitable for amplifying sculpin-type AFPs.

Oligonucleotides for use as probes, e.g., in vitro sculpin-type AFP nucleic acid amplification methods, or for use as nucleic acid probes to detect sculpin-type AFP nucleic acids are typically synthesized chemically according to the solid phase phosphoramidite triester method described by Beaucage and Caruthers (1981), *Tetrahedron Letts.,* 22(20):1859–1862, e.g., using an automated synthesizer, e.g., as described in Needham-VanDevanter et al. (1984) *Nucleic Acids Res.,* 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given sculpin-type AFP nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausbel, Berger, Needham VanDevanter and Mullis (all supra).

Sculpin-type AFP polypeptides of the invention can be synthetically prepared in a wide variety of well-known ways. Sculpin-type AFP polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis,* 2d. ed., Pierce Chemical Co. Sculpin-type AFP polypeptides are also produced by recombinant expression of a nucleic acid encoding the polypeptide followed by purification using standard techniques.

D. Screening for Sculpin-type AFP Nucleic Acids and the Use of Sculpin-type AFP Nucleic Acids as Molecular Probes The nucleic acids of the invention are useful as molecular probes, in addition to their utility in encoding the polypeptides described herein. A wide variety of formats and labels are available and appropriate for nucleic acid hybridization, including those reviewed in Tijssen (1993) *Laboratory Techniques in biochemistry and molecular biology—hybridization with nucleic acid probes* parts I and II, Elsevier, NY and Choo (ed) (1994) *Methods in Molecular Biology Volume 33—In situ Hybridization Protocols* Humana Press Inc., New Jersey (see also, other books in the *Methods in Molecular Biology* series); see especially, Chapter 21 of Choo (id) "Detection of Virus Nucleic Acids by Radioactive and Nonisotopic in situ Hybridization".

For instance, PCR is routinely used to detect sculpin-type AFP nucleic acids in biological samples (see, Innis, supra for a general description of PCR techniques). Accordingly, in one class of embodiments, the nucleic acids of the present invention are used as PCR primers, or as positive controls in PCR reactions (e.g., as templates) for the detection of sculpin-type AFPs in a biological sample such as a cold water fish, or genetically engineered organism comprising a sculpin-type AFP. Briefly, nucleic acids encoded by the nucleic acid constructs of the invention are used as templates to produce oligonucleotides of about 15–25 nucleotides synthetically with sequences similar or identical to a selected sculpin-type AFP nucleic acid subsequence. The oligonucleotides are then used as primers in PCR reactions to detect sculpin-type AFP nucleic acids in biological samples such as an uncharacterized fish-skin extract. The nucleic acids of the present invention (i.e., a nucleic acid corresponding to the region to be amplified) are also used as amplification templates in separate reactions to determine that the PCR reagents and hybridization conditions are appropriate.

Other methods for the detection of nucleic acids in biological samples using nucleic acids of the invention include Southern blots, northern blots, in situ hybridization (including fluorescent in situ hybridization (FISH)), reverse chromosome painting, FISH on DAPI stained chromosomes, generation of Alphoid DNA probes for FISH using PCR, PRINS labeling of DNA, free chromatin mapping and a variety of other techniques described in Choo (supra)). A variety of automated solid-phase detection techniques are also appropriate. For instance, very large scale immobilized polymer arrays (VLSIPS™) are used for the detection of nucleic acids. See, Tijssen (supra), Fodor et al. (1991) *Science,* 251: 767–777 and Sheldon et al. (1993) *Clinical Chemistry* 39(4): 718–719.

Sculpin-type AFP nucleic acids hybridize to probes based upon the nucleotide sequences herein. Using sssAFP2 as example, an oligonucleotide complementary to the 5' (antisense) sequence can be used as probe to screen for skin AFPs in a skin cDNA library. Typically, the probe is used to screen a cDNA or genomic library generated from fish skin using standard techniques (genomic libraries and cDNA libraries are also publicly available from sources known to skilled investigators). Library members (typically bacterial clones or bacterial phage) which hybridize to the antisense oligonucleotide under stringent conditions are selected as AFP candidates. The library members are then sequenced and compared to other skin-type AFPs to verify that they are sculpin-type AFPs.

As such, the present invention relates to an isolated sculpin-type intracellular antifreeze polypeptide encoded by a coding nucleic acid, wherein the coding nucleic acid hybridizes under high-stringency wash conditions to a skin-type antifreeze nucleic acid which encodes sssAFP-2 from shorthorn sculpin or to a second nucleic acid which is complementary to said sculpin-type antifreeze nucleic acid, wherein the coding nucleic acid does not significantly hybridize to an wfsAFP- 1 nucleic acid from Winter flounder under the same high stringency wash conditions.

In this aspect, the skin-type wfsAFP-1 from Winter flounder does not significantly hybridize to a sculpin-type nucleic acid of the present invention, if the signal-to-noise ratio in the hybridization technique is reduced about 25%–40% or more as compared to the binding of a fully complementary sculpin-type AFP. For example, the skin-type wfsAFP-1 from Winter flounder does not hybridize significantly to a sculpin-type nucleic acid of the present invention if the signal-to-noise ratio on a Southern or northern blot is reduced about 25%–40% or more, as compared to the binding of a fully complementary sculpin-type AFP. In a preferred embodiment, the signal-to-noise ratio on a Southern or northern blot is reduced about 40–60% or more, and more preferably, about 60–90% or more as compared to the binding of a fully complementary sculpin-type AFP.

E. Making Conservative Modifications of the Nucleic Acids and Polypeptides of the Invention One of skill will appreciate that many conservative variations of the sequences disclosed yield an essentially identical sculpin-type AFP. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Berger, Needham VanDevanter and Mullis (all supra).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see, Merrifield, and Stewart and Young, supra).

For example, with reference to FIG. 1, the sequence of the first ten amino acid residues of sssAFP-2 is MAAAA-KAAEA (SEQ ID NO:11). Using the conservative substitution table set forth above, this sequence could be MSAAA-KAAEA (SEQ ID NO:12); MASAAKAAEA (SEQ ID NO:13); or MAAAAKAAES (SEQ ID NO:14). In each example, one serine was substituted for one alanine. Other substitutions are possible at one, two or multiple residues.

One of skill can select a desired nucleic acid or polypeptide of the invention based upon the sequences provided and upon knowledge in the art regarding sculpin-type AFPs generally. Moreover, general knowledge regarding the nature of proteins and nucleic acids allows one of skill to select appropriate sequences with activity similar or equivalent to the nucleic acids and polypeptides disclosed in the sequence listings herein. The definition section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, thermal hysteresis, hydrophobicity, ice recrystallization, membrane stability, susceptibility to proteolysis, or the tendency to aggregate are all assayed according to standard techniques.

F. Cloning and Expressing Sculpin-type AFPs

Once a sculpin-type AFP nucleic acid is isolated and cloned, one may express the nucleic acid in a variety of recombinantly engineered cells known to those of skill in the art. Examples of such cells include bacteria, yeast, plant, filamentous fungi, insect (especially employing baculoviral vectors), and mammalian cells. Those of skill in the art are knowledgeable in the numerous expression systems available for cloning and expression of nucleic acids.

In brief summary, the expression of natural or synthetic nucleic acids encoding a sculpin-type AFP is typically achieved by operably linking a nucleic acid encoding the polypeptide of interest to a promoter (which is either constitutive or inducible), and incorporating the construct into an expression vector. The vectors can be suitable for replication and integration in prokaryotes, eukaryotes, or both. Typical cloning vectors contain transcription and translation initiation sequences, transcription and translation terminators, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

(i) Expression in Prokaryotes

To obtain high levels of expression of a cloned nucleic acid, expression vectors will typically contain a strong promoter to direct transcription, a ribosome binding site for translational initiation, and a transcription/translation terminator. For example, as described herein, the polypeptides encoded by sculpin-type AFPs, which are useful, e.g., in protecting cells, tissues and organs against cold, and as antigenic reagents, are optionally expressed in bacterial cells such as *E. coli*. Examples of regulatory regions suitable for this purpose in *E. coli* are the promoter and operator region of the *E. coli* tryptophan biosynthetic pathway as described by Yanofsky, C., 1984, *J. Bacteriol.*, 158:1018–1024 and the leftward promoter of phage lambda ($P_L$) as described by Herskowitz and Hagen, 1980, *Ann. Rev. Genet.*, 14:399–445. The inclusion of selection markers in DNA vectors transformed in bacteria such as *E. coli* is also useful. Examples of such markers include genes specifying resistance to ampicillin, tetracycline, or chloramphenicol. See, Sambrook, Ausbel, and Berger supra, for details concerning selection markers, e.g., for use in *E. coli*. Expression systems for expressing polypeptides are available using *E. coli*, Bacillus sp. (Palva, I. et al., 1983, *Gene* 22:229–235; Mosbach, K. et al., *Nature*, 302:543–545) *lactobacillus* (Chagnaud et al. (1992) *Can. J. Microbiol.* 38: 69–74; Teuber (1993) *Food Reviews International* 9(3): 389–409) *Streptococcus thermophilus* (Mollet et al. (1993) *Journal of Bacteriology* 175(14): 4315–4324; Akahoshi et al. U.S. Pat. Nos. 4,970,083; Klaver et al. 4,938,973) and *Salmonella. E. coli* systems are the most common, and best-defined expression systems and are, therefore, typically preferred. However, in contexts were it is desirable to express sculpin-type AFPs in bacteria used in food production, such as *lactobacillus* (used, e.g., in yogurt and ice cream production), these systems are preferred. Shuttle systems for transferring vectors between *E. coli* and *lactobacillus* are known See, Chagnaud et al. and Teuber et al., both id.

Polypeptides produced by prokaryotic cells often require exposure to chaotropic agents for proper folding. During purification from, e.g., *E. coli*, the expressed protein is optionally denatured and then renatured. This is accomplished, e.g., by solubilizing the bacterially produced polypeptides in a chaotropic agent such as guanidine HCl. The polypeptide is then renatured, either by slow dialysis or by gel filtration. See, U.S. Pat. No. 4,511,503.

(ii) Expression in Eukaryotes

Methods of transfecting and expressing genes in eukaryotic cells are also known in the art and are commercially important For example, transformation of yeast found in frozen dough or bread is of particular use because yeast expressing sculpin-type AFPs have high viability upon thawing, retaining the ability to naturally leaven the dough. Thus, in one preferred embodiment, the sculpin-type AFPs of the invention are expressed in yeast. See, e.g., Sherman et al. (1982) *Methods in Yeast Genetics*, Cold Spring Harbor Laboratory. Examples of promoters for use in yeast include GAL1,10 (Johnson and Davies (1984) *Mol. Cell. Biol.* 4:1440–1448) ADH2 (Russell et al. (1983) *J. Biol. Chem.* 258:2674–2682), PH05 (*EMBO J.* (1982) 6:675–680), and MFα1 (Herskowitz and Oshima (1982) in *The Molecular*

*Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids like YEp6, YEp13, YEp4 can be used as expression vectors. A sculpin-type AFP of interest can be fused to any of the promoters in various yeast vectors. The above-mentioned plasmids have been fully described in the literature (Botstein et al. (1979) *Gene* 8:17–24; Broach, et al. (1979) *Gene,* 8:121–133).

Two procedures are commonly used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen et al. (1978) *Proc. Natl. Acad Sci. USA* 75:1929–1933. The second procedure does not involve removal of the cell wall. Instead the cells are treated, e.g., with lithium chloride or acetate and PEG, and put on selective media (Ito, et al. (1983) *J. Bact.* 153:163–168).

The polypeptides of interest are isolated from yeast (or other cells) by lysing the cells and applying standard protein isolation techniques to the lysates. The polypeptides of this invention are purified to substantial purity by standard techniques well known in the art, including selective precipitation with such substances as ammonium sulfate, column chromatography, immunopurification methods, and others. See, for instance, Scopes (1982) *Protein Purification: Principles and Practice* Springer-Verlag N.Y. The monitoring of the purification process is accomplished by using western blot techniques or radioimmunoassays or other standard immunoassay techniques, or by monitoring the protein directly, e.g., by coomassie blue or silver-stain polyacrylamide gel electrophoresis.

Yet another embodiment is the introduction of sculpin-type AFPs into other cells destined for frozen storage, such as tissue or cell depositories. Illustrative of cells improved by the production of sculpin-type AFPs are cells of fungal, plant, insect or vertebrate (e.g., fish or mammalian) origin. Particularly preferred uses include the transformation of fragile and expensive cell lines such as hybridoma cell lines and tissue culture cell lines. Transforming such cells with sculpin-type AFP nucleic acids is accomplished by various known means. These include calcium phosphate precipitation, fusion of the recipient cells with bacterial protoplasts containing the DNA, treatment of the recipient cells with liposomes containing the DNA, DEAE dextran, receptor-mediated endocytosis, electroporation, microinjection of the DNA directly into the cells, incubating viral vectors containing target nucleic acids which encode polypeptides of interest with cells within the host range of the vector, calcium phosphate transfection, and many other techniques known to those of skill. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein, as well as Sambrook and Ausbel. The culture of cells used in conjunction with the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells. See also, Kuchler et al. (1977) *Biochemical Methods in Cell Culture and Virology*, Kuchler, R. J., Dowden, Hutchinson and Ross, Inc.

As indicated above, the expression vector e.g., a plasmid, which is used to transform the host cell, preferably contains nucleic acid sequences to initiate transcription and sequences to control the translation of the encoded polypeptide. These sequences are referred to generally as expression control sequences. When the host cell is of insect or mammalian origin, illustrative expression control sequences are obtained from the SV-40 promoter (*Science* (1983) 222:524–527), the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for the polypeptide of interest by known means.

As with yeast, when higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VPI intron from SV40 (Sprague et al. (1983) J. Virol. 45: 773–781).

Additionally, gene sequences to control replication in a particular host cell are incorporated into the vector. An example of such sequences are those found in bovine papilloma virus-type vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Va. pp. 213–238.

Sequences controlling eukaryotic gene expression have been extensively studied. Promoter-sequence elements include the TATA-box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers. These sequences are optionally incorporated into the expression vector as part of a characterized heterologous promoter. In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

In one particularly preferred embodiment, the sculpin-type AFPs of the invention are expressed in plant cells, conferring cold resistance to the transformed plant. This has clear value to farmers and other crop producers in cold and temperate climates for the protection of valuable crops such as citrus fruits, tomatoes, strawberries and the like. For expression in plants, a recombinant expression vector will contain, in addition to a sculpin-type AFP sequence, a plant promoter region, a transcription initiation site (if the sequence to be transcribed lacks one), and a transcription termination sequence arranged in an expression cassette. Unique restriction enzyme sites at the 5' and 3' ends of the cassette are typically included to allow for easy insertion into a pre-existing vector.

In plants, further upstream from the TATA box, at positions −80 to −100, there is typically a promoter element with a series of adenines surrounding the trinucleotide G (or T). See, Messing et al., in *Genetic Engineering in Plants*, pp. 221–227 (Kosage, Meredith and Hollaender, eds. 1983). Other sequences conferring tissue specificity, response to environmental signals, or maximum efficiency of transcription are also found in the promoter region. Such sequences are often found within 400 bp of the transcription initiation site, but may extend as far as 2000 bp or more from the start site of transcription.

The particular promoter used in the expression cassette in plants is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. See, Herrara-Estrella et al. (1983), *Nature,* 303:209–213. Viral promoters include the 35S and 19S RNA promoters of cauliflower mosaic virus. See, Odell et al. (1985) *Nature,* 313:810–812. Possible plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer, (1988) *EMBO J.* 7:3315–3327.

Polyadenylation aids in expression of cDNA in plant cells. Polyadenylation sequences include, but are not limited to the Agrobacterium octopine synthase signal (Gielen et al. (1984) *EMBO J,* 3:835–846) and the nopaline synthase signal (Depicker et al. (1982) *Mol. and Appl. Genet,* 1:561–573. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow an a medium containing the particular antibiotic.

Plant expression vectors can be microinjected directly into plant cells by use of micropipettes to mechanically transfer the recombinant DNA. Crossway (1985) *Mol. Gen. Genetics,* 202:179–185. The genetic material may also be transferred into the plant cell using polyethylene glycol. See, Krens, et al. (1982) *Nature,* 296, 72–74. Another method of introduction of expression vectors is high-velocity ballistic penetration by small particles with the nucleic acid either within the matrix of small beads or particles, or on the surface. See, Klein, et al. (1987) *Nature,* 327, 70–73.

Yet another method of introduction in plants is the fusion of protoplasts with other entities, either minicells, cells, lysosomes or other fusible lipid-surfaced bodies. See, Fraley, et al. 1982 *Proc. Natl. Acad. Sci. USA,* 79, 1859–1863. Expression vectors may also be introduced into the plant cells by electroporatiorl See, Fromm et al. (1985) *Pro. Natl. Acad. Sci. USA,* 82:5824. In this technique, plant protoplasts are electroporated in the presence of plasmids containing the expression vector. Electrical impulses of high field strength reversibly permeabilize biomembranes, allowing the introduction of the plasmids. Electroporated plant protoplasts reform the cell wall, divide, and regenerate.

Cauliflower mosaic virus (CaMV) may be used as a vector for introducing the expression vector into plant cells. See, Hohn et al. (1982) *Molecular Biology of Plant Tumors* Academic Press, New York, pp.549–560, and Howell, U.S. Pat. No. 4,407,956. Typically, the CaMV viral DNA genome is inserted into a parent bacterial plasmid, creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

The most preferred vector-mediated method of introducing the expression vector into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. See, J. Schell (1987) *Science,* 237: 1176–1183 and Hoekema, et al. (1983), *Nature,* 303:179–189. All plant cells which can be transformed by Agrobacterium and from which whole plants can be regenerated can be transformed according to the present invention to produce transformed intact plants which contain the desired DNA. See, Hooykas-Van Slogteren et al. (1984), *Nature,* 311:763–764; de la Pena et al. (1987) *Nature* 325:274–276; Rhodes et al (1988) *Science* 240:204–207; Shimamoto et al. (1989) *Nature* 338:274–276. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. 1, 1984, and Vol. III, 1986.

Some suitable plants for transformation by the expression vectors of the present invention include, but are not limited to, species from the genera Fragaria, Lotus, Medicago, Onobrychis, Trifolium, Trigonella, Vigna, Citrus, Limum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhimum, Hererocallis, Nemesia, Pelargonium, Panicum, Pennisetum, Ramunculus, Senecio, Salpiglossis, Cucumis, Browaalia, Glycine, Lolium, Zea, Triticum, Sorghum, Malus, Apium, and Datura, including sugarcane, sugar beet, cotton, fruit trees, and legumes.

In a preferred embodiment, the sculpin-type AFPs are expressed in commercially farmed fish such as catfish and talipia to improve the freeze tolerance of the fish. In this regard, sculpin-type AFP promoters are also useful to target expressed recombinant sculpin-type AFPs to the skin of animals in general and fish in particular. Transgenic fish are generated by microinjection or electroporation of fertilized eggs. Electroporation of fish sperm is also used. See, Fletcher et al. (1988) *Can. J Fish Aquatic Sci.* 45: 352–357, and Gong and Hew (1995) "Transgenic Fish in Aquaculture and Developmental Biology" in *Current Topics in Developmental Biology* 30: 178–214 for a discussion of fish transformation techniques.

In general, the vast majority of AFPs from non-plant sources incorporate a signal peptide that drives their transport from the cytoplasmic space to the cell exterior, thereby providing a protective function that is external to the cell and has limited or no effect on preventing ice crystal formation within the cell itself The skin-derived AFPs of the present invention, have no such signal peptide and are therefore retained within the cell interior of to provide a protective function that is not offered by the secreted isotypes. When used in their native form for the development of cold tolerant phenotypes via transgenesis in xenobiotic species, the extracellular AFPs provide only limited extracellular protection whereas transgenesis via the intracellular isotypes provide superior cold protection that is internal to the cell and is decidedly of greater benefit (e.g., for plants). Therefore, the skin AFPs have potential utility in situ that is clearly distinct from and complementary to the 'classic' secreted AFPs, and as a class can be the preferred choice for the effective development of certain cold-tolerant transgenics that cannot be attained via the transgenetic use of the classic isoforms.

G. Making and Using Antibodies to Sculpin-type Polypeptides

In one embodiment, antibodies are provided which specifically bind to sculpin-type polypeptides. Antibodies can be raised to the polypeptides of the present invention, including individual, allelic, strain, or species variants, and fragments thereof, both in their naturally occurring (full-length) forms and in recombinant forms. Additionally, antibodies can be raised to these polypeptides in either their native configurations or in non-native configurations. Anti-idiotypic antibodies may also be generated. Many methods of making antibodies are known to persons of skill. One of skill will recognize that many variations upon the following methods are known.

i. Antibody Production

A number of immunogens may be used to produce antibodies which specifically bind sculpin-type AFPs. Recombinant or synthetic polypeptides of 10 amino acids in length, or greater, selected from sub-sequences of the skin-type polypeptide provided in SEQ ID NO:2 are preferred polypeptide immunogens for the production of monoclonal or polyclonal antibodies. In one class of preferred embodiments, an immunogenic peptide conjugate is also included as an immunogen. Naturally occurring polypeptides may also be used either in pure or impure form.

Recombinant polypeptides are expressed in eukaryotic or prokaryotic cells and purified using standard techniques, or purified directly from shorthorn sculpin using the techniques described herein. The polypeptide, or a synthetic version thereof, is then injected into an animal capable of producing antibodies. Either monoclonal or polyclonal antibodies are generated for subsequent use, e.g., in immunoassays to measure the presence and quantity of the polypeptide.

Methods of producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, N.Y.; and Harlow and Lane (1989) *Antibodies: A Laboratory Manual* Cold Spring Harbor Press, NY, which are incorporated herein by reference.

Antibodies, including binding fragments and single chain recombinant versions thereof, against predetermined fragments of sculpin-type AFPs can be raised by immunization of animals, e.g., with conjugates of the fragments with carrier proteins as described above. Typically, the immunogen of interest is a peptide of at least about 3 amino acids, more typically the peptide is 5 amino acids in length, preferably, the fragment is 10 amino acids in length and more preferably the fragment is 15 amino acids in length or greater. The peptides are optionally coupled to a carrier protein (e.g., as a fusion protein), or are recombinantly expressed in an immunization vector. Antigeneic determinants on polypeptides to which antibodies bind are typically 3 to 10 amino acids in length.

In addition to polypeptide domains, fusion partners for intracellular sculpin-type AFP subsequences other than polypeptides are also a feature of the invention. Lipids, modified polypeptides, carbohydrates and other moieties are optionally linked to sculpin-type AFP polypeptide subsequences of the invention, e.g., to modify the immunogenicity of the resulting fusion molecule, to facilitate purification of the fusion molecule or to allow for targeting of the molecule. For example, avidin or biotin can be added to a sculpin-type AFP to facilitate purification of the fusion molecule by binding of biotin to avidin. As such, in another embodiment of the present invention, the sculpin-type AFPSs are fusion proteins, where the fusion protein can be chemically or enzymatically modified to generate a mature sculpin-type AFP. For instance, His-sssAFP-2 is but one example of a recombinant fusion protein that can be expressed when a coding nucleic acid is cloned into an expression vector. In this instance, the recombinant protein contained a 20-residue histidine-tag with a single thrombin cleavage site at the N-terminus of the full 92-amino acid residue sequence, to facilitate purification. Another example of fusion protein possessing advantageous properties is wherein the recombinant protein contains an antibody such as a Fab fragment, allowing the sssAFP-fusion protein to target a macromolecular structure, such as a cell surface marker or subcellular compartment. Other fusion proteins links will be well known by those of skill in the art.

Similarly, antibodies or antibody-ligands can be fused to sculpin-type AFP subsequences for purification by binding of antibody to the corresponding ligand or for targeting to specific cells or cellular compartments. Moreover, these fusion proteins comprising antibodies can be used can be used as delivery vehicles to target specific structures within a specific cell or tissue. Many recombinant and chemical techniques for fusion of polypeptide subsequences to additional molecules are known.

Monoclonal antibodies are optionally prepared from cells secreting the desired antibody. These antibodies can be screened for binding to normal or modified polypeptides, or screened for agonistic or antagonistic activity, e.g., activity mediated through a sculpin-type AFP (e.g., thermal hysteresis). Specific monoclonal and polyclonal antibodies will usually bind with a Kd of at least about 0.01 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate host. The polypeptides and antibodies of the present invention are used with or without modification, and include chimeric antibodies such as humanized murine antibodies.

Other suitable techniques involve selection of libraries of recombinant antibodies in phage or similar vectors. See, Huse et al. (1989) "Generation of a Large Combinatorial Library of the Immunoglobulin Repertoire in Phage Lambda," *Science* 246: 1275–1281; and Ward, et al. (1989) *Nature* 341: 544–546.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad Sci. USA* 86: 10029–10033.

The antibodies of this invention can also be used for affinity chromatography in isolating sculpin-type AFPs, or for the identification of AFPs in a biological mixture. Columns can be prepared, e.g., with the antibodies linked to a solid support, e.g., particles, such as agarose, Sephadex, or the like, where a cell lysate is passed through the column, washed, and treated with increasing concentrations of a salt or mild denaturant, whereby purified sculpin-type AFPs are released.

The antibodies can be used to screen expression libraries for sculpin-type AFP expression products. Usually the antibodies in such a procedure will be labeled with a moiety allowing easy detection of presence of antigen by antibody binding.

Antibodies raised against sculpin-type AFPs can also be used to raise anti-idiotypic antibodies. These are usefull for making antibodies with antifreeze properties.

ii. Immunoassays

Sculpin-type AFPs can be detected or measured by a variety of immunoassay methods, including western blots and ELISA analysis. For a review of immunological and immunoassay procedures in general, see Stites and Terr (eds.) 1991 *Basic and Clinical Immunology* (7th ed.). The immunoassays can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier *Science* Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY, and Ngo (ed.) (1988) *Nonisotopic Immunoassays* Plenum Press, NY.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled sculpin-type AFP or a labeled anti-AFP antibody. Alternatively, the labeling agent may be a third moiety, such as another antibody, that specifically binds to the antibody/AFP complex, or to a modified capture group (e.g., biotin) which is covalently linked to the AFP or anti-AFP antibody.

In a preferred embodiments, the labeling agent is an antibody that specifically binds to the capture agent (anti-AFP). Such agents are well known to those of skill in the art, and most typically comprise labeled antibodies that specifically bind antibodies of the particular animal species from which the capture agent is derived (e.g., an anti-idiotypic antibody). Thus, for example, where the capture agent is a mouse derived anti-AFP antibody, the label agent is optionally a goat anti-mouse IgG, ie., an antibody specific to the constant region of the mouse antibody.

Other proteins capable of specifically binding immunoglobulin constant regions, such as streptococcal protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al, *J. Immunol.*, 111: 1401–1406 (1973), and Akerstrom, et al., *J. Immunol.*, 135:2589–2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 5° C. to 45° C.

iii. Generation of Pooled Antisera for Use in Immunoassays.

Sculpin-type AFPs that specifically bind to or that are specifically immunoreactive with an antibody generated against a defined immunogen, such as SEQ ID NO:2, is determined in an immunoassay. The immunoassay uses a polyclonal antiserum which was raised from one sssAFP2. This antiserum is selected to have low cross-reactivity against other AFPs, such as wfsAFP-1 from Winter flounder, and any such cross-reactivity is removed by immunoabsorbtion prior to use in the immunoassay (e.g., by immunosorbtion of the antisera with skin-type polypeptide such as wfsAFP- 1 from Winter flounder.).

In order to produce antisera for use in an immunoassay, the sssAFP2 polypeptide is isolated as described herein. For example, a recombinant sculpin-type AFP, such as sssAFP2, is optionally produced in a cell line, or isolated from shorthorn sculpin fish skin as described in the examples. An inbred strain of mice such as balb/c is immunized with the selected sculpin-type AFP using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogic polypeptide in an immunoassay, for example, a solid-phase immunoassay with the immunogen immobilized on a solid support. Polyclonal antisera with a titer of $10^4$ or greater are selected and tested for their cross reactivity against skin-type AFPs from Winter flounder using a competitive-binding immunoassay such as the one described in Harlow and Lane, supra, at pages 570–573. Preferably two skin-type AFPs (e.g., Winter flounder wfsAFP-1 and Winter flounder wfsAFP-8) are used in this determination in conjunction with the sculpin-type AFP of this invention. In conjunction with sculpin-type AFP of this invention, skin-type AFPs from Winter flounder are used as competitors to identify antibodies which are specifically bound by a sculpin-type AFP of the present invention. The competitive inhibitors can be produced as recombinant proteins and isolated using standard molecular biology and protein chemistry techniques as described herein, or isolated from fish liver using standard techniques.

Immunoassays in a competitive-binding format are typically used for cross-reactivity determinations. For example, the immunogenic polypeptide is immobilized to a solid support. AFPs from Winter flounder added to the assay compete with the binding of the antisera to the immobilized antigen. The ability of the skin-type AFPs from Winter flounder to compete for binding of the antisera to the immobilized protein is compared to the immunogenic polypeptide. The percent cross-reactivity for the above proteins is calculated using standard calculations. Those antisera with less than 10% cross-reactivity with skin-type AFPs from Winter flounder are selected and pooled. The cross-reacting antibodies are then removed from the pooled antisera by immunoabsorbtion with the skin-type AFPs from Winter Flounder.

The immunoabsorbed and pooled antisera are then used in a competitive binding immunoassay as described herein to compare a second "target" AFP to the immunogenic AFP. In order to make this comparison, the two AFPs are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test AFP is specifically bound by the antisera elicited by the immunogenic AFP.

H. Thermal Hysteresis and Related Tests

The effect of the sculpin-type AFPs of the invention on the freezing of aqueous solutions can be assayed using a variety of techniques. Sculpin-type AFPs alter the size of ice crystals formed upon freezing, and the temperature at which water freezes, both in a concentration-dependent manner. Thus, the activity of sculpin-type AFPs are typically tested using one or both of two tests. The first test is an assay for a reduction in crystal size upon rapid freezing. This is performed by dropping serial dilutions of an aqueous solution containing a known amount of sculpin-type AFP onto a cold block of metal and measuring the size of the resulting ice crystals, and recrystallizing ice crystals scraped from the surface of the block. This is the "splat" test, as described, e.g., by Knight et al. (1988) Cryobiology 25: 55–60; Knight and Dugman (1986) Cryobiology 23: 256–262; Knight et al. (1984) Nature 308:295–296 and Warren et al. U.S. Pat No. 5,118,792.

The preferred method of measuring the activity of a sculpin-type AFP is to measure the thermal hysteresis (the difference between the melting and freezing temperatures) of an aqueous solution containing the sculpin-type AFP. This can be done by performing a serial dilution of the sculpin-type AFP-containing aqueous solution, followed by cooling the solution gradually and monitoring the freezing point of the solution. Typically, this is performed using commercially available equipment designed specifically for this purpose, such as nanoliter osmometry. See, Kao et al. (1986) Can. J Zool. 64:578–582. A preferred osmometer is the Clifton Nanolitre Osmometer (Clifton Technical Physics, Hartford, N.Y.). Instructions for using the equipment to perform thermal hysteresis are available from the manufacturer. See also, Chakrabartty et al. (1989) J. Biol. Chem. 264: 11313–11316, for a preferred procedure for measuring thermal hysteresis.

I. Sculpin-type AFPs of the Invention Stabilize Membranes

In another embodiment, the sculpin-type AFPs of this invention protect membranes during cooling, thereby preventing or inhibiting the loss of cellular contents. For instance, when liposomes are cooled to low temperatures, their membranes become leaky, resulting in the loss of intraliposomal contents. The addition of a small amount of sculpin-type AFPs of the present invention stabilizes the membrane, and reduces or inhibits the loss of the contents. Generally, when liposomes are cooled through their transition temperature from liquid crystalline to the gel phase, the intraliposomal contents leak. With the addition of sculpin-type AFPs, the liposome membrane stays intact via stabilization from the sculpin-type AFPs. As such, the present invention relates to a method of stabilizing a membrane, comprising: adding an effective amount of an isolated sculpin-type intracellular antifreeze polypeptide.

The methods are applicable to various membranes. The membranes include, but are not limited to, biological membranes, such as mammalian cells or plant cells, liposomal membranes comprising various lipids, and synthetic polymeric membranes, such as osmotic and dialysis membranes. The sculpin-type AFPs of this invention can be used in the cold storage of platelets, tissues and organs due to their membrane stabilizing abilities. (see, F. Tablin et al., (1996) J. of Cell Physiology, 168:305–313 and L. Hays et al., (1996) Proc. Natl. Acad. Sci. 93:6835–6840). As such, in one embodiment, the present invention provides methods for preserving cells, tissues and organs ex vivo using the sculpin-type AFPs. Preferably, the methods employ sssAFP-2.

One method of measuring membrane stability is to use liposomes loaded with a fluorescent compound, such as carboxyfluorescein, as described in L. Hays et al., (1996) supra. Briefly, fluorescently loaded liposomes are cooled from about 20° C. to about 0° C. at about 0.5° C. a minute. The fluorescence and temperature measurements are recorded by a computer coupled to a fluorometer and thermocouple. When the liposome vesicles becomes leaky, the fluorescent molecule escapes and the fluorescence is recorded. In this manner, the inhibition of leaky vesicles or membrane stabilizing effect of sculpin-type AFPs can be determined.

J. Inhibition of Ice Recrystallization and Additional Uses for the Sculpin-type AFPs of the Invention As described herein, the sculpin-type AFPs of the invention depress the freezing point of aqueous solutions in a concentration-dependent manner. Accordingly, the sculpin-type AFPs of the invention are generally useful in inhibiting solutions from freezing. This improves the shelf life of many refrigerated foods, making the foods more palatable. In the case of cold, viscous liquids such as soft-serve ice creams and frozen yogurt, various emulsifiers are used to keep the components of the liquid in solution. The sculpin-type AFP, when added, inhibits ice recrystallization during cold storage, improving the texture and palatability of the food.

Ice recrystallization can be assayed using the "splat cooling" assay as described by Knight et al., (1988), *Cryobiology*, 25:55–60. Alternatively, ice recrystallization can be assessed by measuring the "hysteresis gap" as described by Knight et al., (1984), *Nature*, 308:295–296. Briefly, the equilibrium freezing point of a solution of sculpin-type AFP can be obtained by dispersing an AFP solution within a thin glass frit, then weighing the frit after it reaches equilibrium with ice at a constant temperature in an atmosphere of pure water vapor. The freezing hysteresis (the lowering of the freezing point) represents the inhibition of freezing by the sculpin-type AFP. (see, Knight et al., (1984), supra).

Cells which express the sculpin-type AFPs of the invention are more cold-tolerant than counterpart cells which do not express sculpin-type AFPs. This is due to freezing point depression of the intracellular compartment, and prevention of cellular dehydration and osmotic damage. Thus, the sculpin-type AFPs of the invention are used to improve the cold tolerance of bacteria, cell cultures, plants and animals. This has many useful commercial applications in medicine, agriculture and aquaculture. For instance, cold-resistant plants have a longer growing season in temperate and northern climates than their ordinary counterparts. This allows for higher crop yields, and protects crops against unanticipated early frosts. Essentially any crop grown in a temperate or northern climate is improved by increased cold resistance. In particular, citrus crops such as oranges, grapefruit, lemons and tangerines benefit from cold resistance, as do tomatoes, tobacco, potatoes, legumes and the like.

In a preferred embodiment, sculpin-type AFPs are expressed in medically valuable cell lines such as hybridoma lines to improve the freeze tolerance of the cell lines.

Sculpin-type AFPs also have certain antibacterial properties, providing a means of unwanted reducing bacteria in foods such as recombinant fruits expressing Sculpin-type AFPs, and in blended food stuffs such as ice creams. This improves shelf life, food quality, and makes such products safer for consumption.

EXAMPLES

The following examples are provided by way of illustration only and not by way of limitation. Those of skill will readily recognize a variety of noncritical parameters which can be changed or modified to yield essentially similar results.

Materials and Methods

The following materials and methods were used in examples set forth below.

A. Tissue Collection

Tissues from shorthorn sculpin (*Myoxocephalus scorpius*) were collected from Conception Bay, Newfoundland, Canada. The tissues of freshly killed fish were collected and stored in liquid nitrogen, shipped on dry ice, and stored at −70° C. before use.

B. Library Construction and Screening

Total skin RNA from a shorthorn sculpin collected on May 30, 1995 was isolated by acid guanidium thiocyanate-phenol-chloroform extraction as described by Gong et al. (see, Gong, Z. et al. (1992) *Can. J. Zool.* 70, 810–814). Skin Poly(A+) RNA was obtained using a Micro-FastTract™ mRNA isolation kit (Invitrogen®, San Diego, Calif.). A skin cDNA library was constructed and screened as described by the manufacturer using a ZAP-cDNA® synthesis kit and Uni-ZAPt™ Cloning kit (Stratagene® La Jolla, Calif.). Nylon membranes (Colony/Plaque Screen™, DuPont, Biotechnology Systems/NEN Research Products, Boston, Mass.) were hybridized in a buffer of 4×SET (0.6 M NaCl, 120 mM Tris, pH 8.0, 8 mM EDTA), 0.4% NaPP$_i$, 25 mM PB buffer, 0.5% SDS, 9% dextran sulphate, 50% formamide, 250 mg/mL denatured calf thymus DNA and ~0.5×10$^6$ cpm/mL of probe, at 42° C. for 15 hr. Probe was labeled with $\alpha$-$^{32}$P-dATP or dCTP using a Random Primers DNA Labeling System kit (Life Technologies, Gaithersburg, Md.). The final wash was performed in 0.2×SSC (30 mM NaCl, 30 mM Sodium Citrate, pH 7.0), and 0.5 % SDS, at 50° C. for 15 min. A 260 bp clone corresponding to Winter flounder skin AFP (see, Gong, Z. et al. (1996) *J. Biol. Chem.* 271, 4106–4112) was used as a probe to screen approximately 6.0×10$^4$ clones of the primary library. DNA sequencing was performed using a double-stranded Nested Deletion Kit (Pharmacia Biotech, Baie d'Urfé, Que.).

C. Northern Analysis

Total RNA from various tissues of three shorthorn sculpin were isolated using TRIZOL™ Reagent as described by the manufacturer (Life Technologies). Five mg of total RNA from each tissue were separated in a denaturing (37% formaldehyde) 1.3% agarose gel, transferred to Hybond™-N (Amersham Life Science, Cleveland, Ohio) nylon membranes, and UV-crosslinked. The hybridization solution consisted of 40% formamide, 5% dextran sulfate, 4×SSC, 7 mM Tris pH 7.5, 1% SDS, 1×DenHardt's buffer, 100 mg/mL denatured calf thymus DNA and ~1.0×10$^6$ cpm/mL of labeled probe. A PstI/SmaI digested fragment of the s3-2 3'-UTR (437 bp), that included the last 15 bp of the ORF but lacked the poly(A+) tail, was used as the probe. Both calf thymus DNA and probe were heat denatured before use. Hybridization was performed at 60° C. with overnight incubation. Washing conditions began at room temperature and finished at 72° C. in solutions ranging from 1×SSC-1% SDS to 0.1×SSC–0.1% SDS-with 15 min. incubations in each solution. The signal was identified by autoradiography.

D. Reverse Transcriptase-PCR

One mg of total RNA from various tissues was combined with 0.5 mg of a primer, 5'-AGCTCCGGTCTGAACT TCAA-3' (SEQ ID NO:15), complimentary to a region in the 3'-UTR of s3-2. Reverse transcription was performed using M-MLV RT as described by the manufacturer (Life Technologies). One tenth of the RT mixture was PCR amplified using the same primer plus a second primer, 5'-TGCGTAGCAGTGTCTCCGTA-3' (SEQ ID NO:16), corresponding to the 3'-UTR region adjacent to the ORF. The amplification consisted of cycles at 94° C. (60 sec), 70° C. (90 sec), and 72° C. (105 sec). PCR products were resolved in a 1.2% agarose gel with EtBr staining. The identity of the products was confirmed by Southern blotting and hybridization with the 437 bp 3'-UTR probe.

E. Primer Extension

A 22-mer primer complimentary to the 5'-end of s3-2, 5'-CAACAACTTCCTGATGAGTCAC-3'(SEQ ID NO:17), was synthesized and labeled with γ-$^{32}$P-dATP by T4 polynucleotide kinase (New England Biolabs, Beverly, Mass.) to a specific activity of ~1.0×10$^5$ cpm/ng. Primer extension was performed as described by Boorstein and Craig (Boorstein, W. R. et al. (1989) *Methods in Enzymology* 180: 347–369) using M-MLV RT (Life Technologies) Primer extension products were precipitated with EtOH and sodium acetate, redissolved in formamide loading buffer, separated in a denaturing polyacrylamide gel, and visualized by autoradiography.

F. Construction of pET-15b-s3-2

PCR primers were designed in accordance with the s3-2 cDNA sequence and the cloning sites of pET System expression vector pET-15b (Novagen, Madison, Wis.); 5'-GCGGC AGCCATATGGCGGCGGCGGCGAAG-3' (SEQ ID NO:18) (upper strand), 5'-GCAGCCGGATCCTCGAGA CACTGCTACGC-3'(lower strand) (SEQ ID NO:19), where the underlined regions represent the NdeI and BamHI XhoI restriction sites. PCR was performed using pfu DNA polymerase (Stratagene®). The amplification procedure consisted of 20 cycles at 98° C. (45 sec), 66° C. (20 sec) and 78° C. (60 sec). The resultant 313 bp PCR-synthesized fragment and pET-15b vector were both double digested with NdeI and BamfHI, recovered from low-melting temperature agarose gel (FMC BioProducts, Rockland, Me.), and ligated using T4 DNA ligase (Pharmacia Biotech). Initial cloning work was performed in DH5a cells (*E. coli*) and sequence of the insert was confirmed by using a T7 Sequencing kit™. (Pharmacia Biotech).

G. Expression and Purification of His-sssAFP-2 Recombinant Protein

Induced expression of the recombinant protein (His-sssAFP-2) was performed in 1 L of BL21(DE3) cells as described by the manufacturer (Novagen, Madison, Wis.). Bacteria cells were harvested by centrifugation at 5000×g for 5 min. and the cell pellet was re-suspended in 4 mL of ice-cold binding buffer, (5 mM imidazole, 0.5 M NaCl and 80 mM Tris-HCl, pH 7.9)/100 mL of cell paste. The bacterial pellet was subjected to ultrasound sonication and cell debris was removed by centrifugation. The supernatant was loaded onto a pre-packed and equilibrated Ni$^{2+}$ column. Recombinant protein was then purified and eluted according to the manufacturer's instructions (Novagen). Following dialysis in 0.1M NH$_4$HCO$_3$ and lyophilization, the sample was further purified by C$_{18}$ reverse-phase HPLC. The purified protein was subjected to SDS-PAGE, amino acid analysis, protein sequencing, and mass spectroscopy. Amino acid analysis and protein sequencing were performed by the Biotechnology Service Centre, Hospital for Sick Children, Toronto, and mass spectrometry was performed by the Carbohydrate Centre, University of Toronto, Toronto.

H. Circular Dichroism Spectroscopy

Lyophilized His-sssAFP-2 was dissolved in 0.01M PB buffer, pH 7.0. CD measurement was carried out at 0° C. using a cuvette of 0.1 cm path length. The final CD spectrum is an average of the mean residue ellipticities as calculated for three concentrations, 0.145, 0.098, and 0.065 mg/mL.

The equation;

$$[\theta]^r = [\theta]^\circ (1 - k/n)$$

where n is the chain length and k is a wavelength-dependent factor (2.57 at 222 nm) and $[\theta]^{\infty} = -39,500$ degree·cm$^2$·dmol$^-$was used to caluclate the predicted man residue ellipticity for 100% helix. The percentage of helix for His-sssAFP-2 was determined from the average mean residue ellipticity at 222 nm.

I. Measurement of Antifreeze Activity

Antifreeze activity was measured as thermal hysteresis following the procedure of Chakrabartty et. al. (see, A. Chakrabartty et al. (1989) *J. Biol. Chem.* 264, 11313–11316), using a Clifton Nanolitre Osmometer (Clifton Technical Physics, Hartford, N.Y.). Both control (wflAFP-6, Winter flounder liver type AFP) and His-sssAFP-2 were dissolved in 0.1 M NH$_4$HCO$_3$ and centrifuged and diluted to desired concentrations before use. For each dilution, measurements were made from three wells, and the average value taken.

Example 1

This example illustrates the isolation of a skin-type AFP cDNA clone.

To investigate the presence of AFPs in the skin of shorthorn sculpin, a skin cDNA library was constructed and screened under low stringency conditions (0.6 M NaCl, 42° C.) using a Winter flounder skin-type AFP clone (Gong, Z. et al. (1996) *J. Biol. Chem.* 271, 4106–4112). Two clones, s3-2 (1027 bp) (SEQ ID NO:1) and s17-12 (991 bp) (SEQ ID NO:3) which contained complete ORF of alanine-rich peptides were isolated. Sequence comparisons of s17-12 and s3-2 showed that the two clones were identical, with s3-2 containing an additional 36 bp of the 5'-untranslated region.

The 276 bp ORF of s3-2 encodes an alanine-rich polypeptide of 92 residues which was designated as sssAFP-2 (shorthorn sculpin skin AFP) (see, FIG. 1). Similar to the skin-type AFP isolated from Winter flounder (Gong, Z. et al., supra) the cDNA sequence of s3-2 does not possess a signal peptide or any presumptive prosequences. Comparisons of portions of the sssAFP-2 sequence with various Type I AFPs gives identities of around 50% to 60%. This is due to the fact that all the Type I AFPs contain approximately 60% alanine.

Example 2

This example illustrates the tissue distribution and seasonal variation of skin-type AFP mRNA.

Total RNA from skin, liver, brain, and the dorsal fin of three shorthorn sculpin were investigated by northern blot analysis. Hybridization with a 437 bp fragment of the 3'-UTR of s3-2 produced bands in the skin, brain, and dorsal fin samples of approximately 1.1 kb in size. Notably absent were positive signals from three liver AFPs run along side for comparison. Probing of the same blot with the ORF of s3-2 produced similar results, i.e., ~1.1 kb bands in skin, brain, and dorsal fin and absence in liver. The strongest signal in all tissues was observed from the fish collected in the month of March and the weaker signals were observed for skin and dorsal fin collected in May. The lowest levels were found in the samples collected in September. These findings indicate that the skin-type AFP mRNA levels exhibit significant seasonal variation.

A wider range of tissues were further investigated by reverse transcriptase-PCR. Positive signals were clearly detected from 1 mg of gill filament, skin, dorsal fin, brain, and stomach total RNA. Furthermore, weaker positive signals were seen in the kidney and muscle samples. However, the signal, as expected, was absent in the liver. The identity of the RT-PCR products was further confirmed by Southern analysis. Primer extension studies were carried out to determine the complete length of the s3-2 clone and to further confirm its tissue-specific expression The results indicated that there were three major primer extension products at approximately 91–95 nt in length, which indicates that the entire s3-2 clone would be approximately 1090 bp in length, which in turn correlated well with the predicted size of 1.1 kb determined in northern analysis. The three bands were easily detected in as little as 0.5 mg of skin total RNA, but not in 20 mg of liver RNA, which further confirmed that sssAFP-2 is not produced in the liver. These results indicate that sssAFP-2 mRNA expression is seasonally regulated and is widely expressed in many tissues.

Example 3

This example illustrates the properties of the recombinant protein His-sssAFP-2.

To further study the structure and function of sssAFP-2, the 276 bp ORF of s3-2 was cloned into an expression vector, pET-15b. The recombinant protein (designated as His-sssAFP-2) contained a 20-residue histidine-tag with a single thrombin cleavage site at the N-terminus of the full 92-residue sequence. The protein was soluble and purified from the cell extract using a $Ni^{2+}$ column and reverse-phase HPLC. The identity of the purified protein was confirmed by amino acid analysis, protein sequencing and mass spectrometry. Mass spectrometry produced an estimated protein mass of 9723.46 with a standard deviation of 1.75 which is in agreement with the mass predicted from the amino acid sequence. In the CD spectrum, His-sssAFP-2 displayed minimums at 208 and 222 nm, which are indicative of an α-helical structure and the percent helix was calculated to be 74% at 0° C. (see, FIG. 3, A&B).

The thermal hysteretic activity of His-sssAFP-2 was concentration-dependent (see, FIG. 2, A&B) and it produced the typical bipyramidal ice crystals found with other AFPs. Furthermore, at higher concentrations of His-sssAFP-2, the crystals became elongated and approached needle-like structures, a property that is characteristic of active AFPs.

All publications, patent applications, patents and other references cited or listed herein are incorporated by reference. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An isolated sculpin-type intracellular antifreeze polypeptide, said polypeptide comprising at least four Pr-X$_2$-Pr-X$_7$ subsequences, wherein:

Pr is a polar amino acid selected from the group consisting of: serine, asparagine, glutamine, tyrosine, cysteine, lysine, arginine, histidine, aspartic acid, and glutamic acid;

X is a member independently selected from the group consisting of amino acids;

said polypeptide comprises at least about 50% alanine;

said polypeptide induces a concentration-dependent decrease in the freezing point of an aqueous solution.

2. An isolated sculpin-type intracellular antifreeze polypeptide in accordance with claim 1, wherein said polypeptide comprises at least six Pr-X$_2$-Pr-X$_7$ subsequences, wherein at least two of said subsequences overlap.

3. An isolated sculpin-type intracellular antifreeze polypeptide in accordance with claim 1, wherein said polar amino acid is a member independently selected from the group consisting of asparagine, aspartic acid, glutamic acid, and lysine.

4. An isolated sculpin-type intracellular antifreeze polypeptide in accordance with claim 1, wherein X is an amino acid independently selected from the group consisting of alanine, serine, valine, glutamic acid, threonine, methionine and lysine.

5. An isolated sculpin-type intracellular antifreeze polypeptide in accordance with claim 1, wherein at least 40% of X in each of said at least four Pr-X$_2$-Pr-X$_7$ subsequences are alanine.

6. An isolated sculpin-type intracellular antifreeze polypeptide in accordance with claim 1, wherein said polypeptide comprises at least about 60% alanine.

7. An isolated sculpin-type intracellular antifreeze polypeptide in accordance with claim 1, wherein said polypeptide has a molecular weight of about 7900 DA to about 9700 DA.

8. An isolated sculpin-type intracellular antifreeze polypeptide in accordance with claim 1, wherein said polypeptide is a fusion protein.

9. An isolated sculpin-type intracellular antifreeze polypeptide in accordance with claim 8, wherein said fusion protein can be chemically or enzymatically modified to generate an AFP.

10. An isolated sculpin-type intracellular antifreeze polypeptide in accordance with claim 8, wherein said fusion protein contains a proteolytic cleavage site.

11. An isolated sculpin-type intracellular antifreeze polypeptide in accordance with claim 9, wherein said polypeptide has a single thrombin cleavage site at the N-terminus.

12. An isolated sculpin-type intracellular antifreeze polypeptide in accordance with claim 1, wherein said polypeptide is between about 45 to about 100 amino acids in length.

13. An isolated sculpin-type intracellular antifreeze polypeptide in accordance with claim 1, wherein said polypeptide is at least about 70% α-helical as measured by circular dichroism at about 0° C.

14. An isolated sculpin-type intracellular antifreeze polypeptide in accordance with claim 1, wherein said polypeptide is sssAFP-2 from shorthorn sculpin.

15. A composition comprising an isolated sculpin-type intracellular antifreeze polypeptide in accordance with claim 1.

16. An isolated sculpin-type intracellular antifreeze polypeptide in accordance with claim 1, wherein said isolated polypeptide depresses the freezing point of water in a concentration dependent manner.

17. An isolated sculpin-type intracellular antifreeze polypeptide in accordance with claim 1, wherein said isolated polypeptide inhibits ice formation and recrystallization.

18. An isolated sculpin-type intracellular antifreeze polypeptide in accordance with claim 1, wherein said isolated polypeptide stabilizes a membrane.

19. An isolated sculpin-type intracellular antifreeze polypeptide in accordance with claim 1, wherein said polypeptide binds to a pool of polyclonal antibodies, wherein the polyclonal antibodies of the pool are polyclonal antibodies raised against the sssAFP-2 polypeptide from shorthorn sculpin and subtracted with an wfsAFP-1 polypeptide from Winter flounder.

20. A method of making an aqueous composition resistant to freezing, said method comprising: adding the sculpin-type antifreeze polypeptide in accordance with claim 1 to the composition in an amount sufficient to cause thermal hysteresis of the composition.

21. A method of inhibiting ice recrystallization in a composition, said method comprising: adding an effective amount of a sculpin-type intracellular antifreeze polypeptide in accordance with claim 1 to said composition, thereby inhibiting ice formation or recrystallization in the composition.

22. A method of inhibiting ice recrystallization in a composition in accordance to claim 20, wherein said polypeptide is sssAFP-2 from shorthorn sculpin.

* * * * *

SEQUENCE LISTING

<160> NUMBER OF SEQ ID NOS: 19

<210> SEQ ID NO 1
<211> LENGTH: 1027
<212> TYPE: DNA
<213> ORGANISM: Myoxocephalus scorpius
<220> FEATURE:
<223> OTHER INFORMATION: cDNA clone s3-2
<220> FEATURE:
<221> NAME/KEY: CDS
<222> LOCATION: (66)..(344)
<223> OTHER INFORMATION: shorthorn sculpin skin-type antifreeze
      polypeptide (sssAFP-2)

<400> SEQUENCE: 1

```
gtgactcatc aggaagttgt tgatctttct ctgttccaaa cgcaccgagc taaacaaaag        60 tgaga atg gcg gcg gcg gcg aag gcg gcg gag gcg gcg gca atg gcg gcg      110
      Met Ala Ala Ala Ala Lys Ala Ala Glu Ala Ala Ala Met Ala Ala
      1               5                  10                  15 gca aat gcg gcg gag gcg gcg gca acg aag gcg gct gat gcg gct gcg        158
Ala Asn Ala Ala Glu Ala Ala Ala Thr Lys Ala Ala Asp Ala Ala Ala
                20                  25                  30 tcg gcg gca gct gcg gct att gcg gct att gcg gag gcg gcg gag gcg        206
Ser Ala Ala Ala Ala Ala Ile Ala Ala Ile Ala Glu Ala Ala Glu Ala
            35                  40                  45 gcg gag gca gcg gca acg aag tcg gct aat gta gcg gcg gcg gcg gca        254
Ala Glu Ala Ala Ala Thr Lys Ser Ala Asn Val Ala Ala Ala Ala Ala
        50                  55                  60 gcg acg tcg gcc gcg gca gca gcg aag gct acg gct aat gcg gca gcg        302
Ala Thr Ser Ala Ala Ala Ala Lys Ala Thr Ala Asn Ala Ala Ala
    65                  70                  75 gca gca tca gca gct gca gca gct gca gca gca gtt gcg tagcagtgtc         351
Ala Ala Ser Ala Ala Ala Ala Ala Ala Ala Val Ala
80                  85                  90 tccgtagagc agttggctgc ttataatgct cgatatgtgg caacaaacat agttaatttg      411
ttcagtaatg cacaagttac actataaggt tcttttaggg tgtgggtagt tggctgctct      471
ttgatttatg aatgacaaat tgggatttta tggtttgtcc atgcttaatt cttaatccct      531
```

-continued

```
gatgttgctg acccaactca gtgtggtgct tgtttatgtt gctgaatatc acaggttatt      591
aatacgtaaa ttcaagtatg aacacacat gttattttgt tgttgtgaga aacacattca       651
atcaaacaaa aagcatcttg agacgctcct gttgtgaatc agtataatca atttaaatgt      711
gtggttaaaa actcactgct taatctcat aaccaagaaa tgcttttaca gcccgggaaa       771
agtgaacctc cacaaagatc tttctttaga gctaatgtag tagcttaaag atctcatcag      831
tgttgatgag caaagtcgtt ggtgaacaaa ctgtacctct ttaaaaacgt tttgaagttc      891
agaccggagc taaaactccc attatctcc atctggttat tgaaaatgt tgtgatttgg        951 gtgatttggg tgaattaaaa gaacctctat aaacaaaaaa aaaaaaaaa aaaaaaaaa       1011 aaaaaaaaaa aaaaa                                                     1027
```

<210> SEQ ID NO 2
<211> LENGTH: 92
<212> TYPE: PRT
<213> ORGANISM: Myoxocephalus scorpius

<400> SEQUENCE: 2

```
Met Ala Ala Ala Ala Lys Ala Ala Glu Ala Ala Met Ala Ala
 1               5                  10                  15

Asn Ala Ala Glu Ala Ala Ala Thr Lys Ala Ala Asp Ala Ala Ser
            20                  25                  30

Ala Ala Ala Ala Ala Ile Ala Ala Ile Ala Glu Ala Ala Glu Ala Ala
            35                  40                  45

Glu Ala Ala Ala Thr Lys Ser Ala Asn Val Ala Ala Ala Ala Ala
            50                  55                  60

Thr Ser Ala Ala Ala Ala Ala Lys Ala Thr Ala Asn Ala Ala Ala Ala
 65                  70                  75                  80

Ala Ser Ala Ala Ala Ala Ala Ala Ala Ala Val Ala
                85                  90
```

<210> SEQ ID NO 3
<211> LENGTH: 991
<212> TYPE: DNA
<213> ORGANISM: Myoxocephalus scorpius
<220> FEATURE:
<223> OTHER INFORMATION: cDNA clone s17-12
<220> FEATURE:
<221> NAME/KEY: CDS
<222> LOCATION: (30)..(308)
<223> OTHER INFORMATION: shorthorn sculpin skin-type antifreeze
      polypeptide (sssAFP-2)

<400> SEQUENCE: 3

```
caaacgcacc gagctaaaca aaagtgagaa tggcggcggc ggcgaaggcg gcggaggcgg       60
cggcaatggc ggcggcaaat gcggcggagg cggcggcaac gaaggcggct gatgcggctg      120
cgtcggcggc agctgcggct attgcggcta ttgcggaggc ggcggaggcg gcggaggcag      180
cggcaacgaa gtcggctaat gtagcggcgg cggcggcagc gacgtcggcc gcggcagcag      240
cgaaggctac ggctaatgcg gcagcggcag catcagcagc tgcagcagct gcagcagcag      300
ttgcgtagca gtgtctccgt agagcagttg gctgcttata atgctcgata tgtgcaaca      360 aacatagtta atttgttcag taatgcacaa gttacactat aaggttcttt tagggtgtgg      420
gtagttggct gctctttgat ttatgaatga caaattggga ttttatggtt tgtccatgct      480
taattcttaa tccctgatgt tgctgaccca actcagtgtg tgcttgttt atgttgctga       540 atatcacagg ttattaatac gtaaattcaa gtatggaaca cacatgttat tttgttgttg      600
```

```
tgagaaacac attcaatcaa acaaaaagca tcttgagacg ctcctgttgt gaatcagtat       660
aatcaattta aatgtgtggt taaaaactca ctgcttaaat ctcataacca agaaatgctt       720
ttacagcccg ggaaaagtga acctccacaa agatctttct ttagagctaa tgtagtagct       780
taaagatctc atcagtgttg atgagcaaag tcgttggtga acaaactgta cctctttaaa       840
aacgttttga agttcagacc ggagctaaaa ctcccattta tctccatctg gttattgaga       900
aatgttgtga tttgggtgat ttgggtgaat taaaagaacc tctataaaca aaaaaaaaa       960 aaaaaaaaaa aaaaaaaaaa aaaaaaaaaa a                                     991

<210> SEQ ID NO 4
<211> LENGTH: 37
<212> TYPE: PRT
<213> ORGANISM: Pleuronectes americanus
<220> FEATURE:
<223> OTHER INFORMATION: Winter flounder liver-type antifreeze
      polypeptide (wflAFP-6)

<400> SEQUENCE: 4

Asp Thr Ala Ser Asp Ala Ala Ala Ala Ala Leu Thr Ala Ala Asn
 1               5                  10                  15

Ala Lys Ala Ala Ala Glu Leu Thr Ala Ala Asn Ala Ala Ala Ala
                20                  25                  30

Ala Ala Thr Ala Arg
            35

<210> SEQ ID NO 5
<211> LENGTH: 38
<212> TYPE: PRT
<213> ORGANISM: Pleuronectes americanus
<220> FEATURE:
<223> OTHER INFORMATION: Winter flounder skin-type antifreeze
      polypeptide (wfsAFP-1)

<400> SEQUENCE: 5

Met Asp Ala Pro Ala Arg Ala Ala Ala Ala Thr Ala Ala Ala Ala Lys
 1               5                  10                  15

Ala Ala Ala Glu Ala Thr Lys Ala Ala Ala Lys Ala Ala Ala Ala
                20                  25                  30

Thr Lys Ala Ala Ala His
            35

<210> SEQ ID NO 6
<211> LENGTH: 241
<212> TYPE: DNA
<213> ORGANISM: Pleuronectes americanus
<220> FEATURE:
<223> OTHER INFORMATION: Winter flounder skin-type antifreeze polypeptide
      (wfsAFP-1) nucleic acid

<400> SEQUENCE: 6
actgtcgacc actcagaatc actgacatca acatggacgc accagccaga gccgccgcag        60
ccaccgccgc cgccgccaag gccgccgcag aagccaccaa agccgcagcc gccaaagcag       120
cagctgccac caaagccgca gcccattaat gatcgtggtc gtcttgatgt gggatcatgt       180
gaacatctga gcagccagat gttaccaatc tgctgaataa acctgagaag ctgtttgttg       240
a                                                                      241

<210> SEQ ID NO 7
<211> LENGTH: 322
```

```
<212> TYPE: DNA
<213> ORGANISM: Pleuronectes americanus
<220> FEATURE:
<223> OTHER INFORMATION: Winter flounder liver-type antifreeze
      polypeptide (wflAFP-6) nucleic acid

<400> SEQUENCE: 7
accacatctt cattttgtag tgaaccagtg ctccctacaa gttctcaaaa tggctctctc      60
acttttcact gtcggacaat tgattttctt attttggaca atgagaatca ctgaagccag     120
ccccgacccc gcagccaaag ccgccccagc agcagctgcc gccctgccg cagccgcccc      180 agacaccgcc tctgacgccg ccgctgcagc cgcccttacc gccgccaatg ccgccgccgc     240
cgccaaactc accgccgaca acgccgccgc cgccgcagca gccaccgcca gaggttaagg     300
atcgtggtcg tcttgatgtg gg                                              322

<210> SEQ ID NO 8
<211> LENGTH: 292
<212> TYPE: DNA
<213> ORGANISM: Pleuronectes americanus
<220> FEATURE:
<223> OTHER INFORMATION: Winter flounder skin-type antifreeze
      polypeptide (wfsAFP-8) nucleic acid

<400> SEQUENCE: 8
ttcactgtcg aacactcaga atcactgaca tcaacatgga cgcaccagcc gccgccgccg      60
cagccaccgc cgccgccgcc aaggccgccg cagaagccac cgcagctgcc gcagccgcag     120
ccgccgcagc cactgccgaa gccgccgcca aagcagccgc cgccaccaaa gccgcagccg     180
ccgcagccgc cgcccgttaa ggatcatcgt cgtcttgctg taaaatcatg tgaacatctg     240
agcagcgaga tgtcaccaat ctgttgaatg gggctgagaa gctgtttgtt ta             292

<210> SEQ ID NO 9
<211> LENGTH: 11
<212> TYPE: PRT
<213> ORGANISM: Myoxocephalus scorpius
<220> FEATURE:
<221> NAME/KEY: PEPTIDE
<222> LOCATION: (1)..(11)
<223> OTHER INFORMATION: second 11 amino acid sculpin-type AFP
      subsequence

<400> SEQUENCE: 9

Asn Ala Ala Glu Ala Ala Ala Thr Lys Ala Ala
  1               5                  10

<210> SEQ ID NO 10
<211> LENGTH: 11
<212> TYPE: PRT
<213> ORGANISM: Myoxocephalus scorpius
<220> FEATURE:
<221> NAME/KEY: PEPTIDE
<222> LOCATION: (1)..(11)
<223> OTHER INFORMATION: third 11 amino acid sculpin-type AFP
      subsequence

<400> SEQUENCE: 10

Lys Ala Ala Asp Ala Ala Ala Ser Ala Ala Ala
  1               5                  10

<210> SEQ ID NO 11
<211> LENGTH: 10
<212> TYPE: PRT
<213> ORGANISM: Myoxocephalus scorpius
<220> FEATURE:
```

```
<221> NAME/KEY: PEPTIDE
<222> LOCATION: (1)..(10)
<223> OTHER INFORMATION: first ten amino acid residues of sssAFP-2

<400> SEQUENCE: 11

Met Ala Ala Ala Ala Lys Ala Ala Glu Ala
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:first ten
      amino acid residues of sssAFP-2 with conservative substitution of
      Ser for Ala at position 2

<400> SEQUENCE: 12

Met Ser Ala Ala Ala Lys Ala Ala Glu Ala
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:first ten
      amino acid residues of sssAFP-2 with conservative substitution of
      Ser for Ala at position 3

<400> SEQUENCE: 13

Met Ala Ser Ala Ala Lys Ala Ala Glu Ala
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:first ten
      amino acid residues of sssAFP-2 with conservative substitution of
      Ser for Ala at position 10

<400> SEQUENCE: 14

Met Ala Ala Ala Ala Lys Ala Ala Glu Ser
 1               5                  10

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:reverse
      transcriptase-PCR primer complementary to a region in the 3'-UTR
      of s3-2

<400> SEQUENCE: 15
agctccggtc tgaacttcaa                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:reverse
      transcriptase-PCR second primer corresponding to the 3'-UTR region
      adjacent to the ORF

<400> SEQUENCE: 16
```

-continued

```
tgcgtagcag tgtctccgta                                          20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:22-mer
      primer complimentary to the 5'-end of s3-2

<400> SEQUENCE: 17
caacaacttc ctgatgagtc ac                                       22

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:upper strand
      PCR primer

<400> SEQUENCE: 18
gcggcagcca tatggcggcg gcggcgaag                                29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:lower strand
      PCR primer

<400> SEQUENCE: 19
gcagccggat cctcgagaca ctgctacgc                                29
```